(12) United States Patent
Sharma et al.

(10) Patent No.: US 11,967,305 B2
(45) Date of Patent: *Apr. 23, 2024

(54) AMBIENT COOPERATIVE INTELLIGENCE SYSTEM AND METHOD

(71) Applicant: Nuance Communications, Inc., Burlington, MA (US)

(72) Inventors: Dushyant Sharma, Mountain House, CA (US); Patrick A. Naylor, Reading (GB); Joel Praveen Pinto, Aachen (GB); Daniel Paulino Almendro Barreda, London (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/840,958

(22) Filed: Jun. 15, 2022

(65) Prior Publication Data

US 2022/0310055 A1 Sep. 29, 2022

Related U.S. Application Data

(63) Continuation of application No. 17/077,863, filed on Oct. 22, 2020, now Pat. No. 11,398,216.

(Continued)

(51) Int. Cl.
*G10L 13/02* (2013.01)
*G06F 3/16* (2006.01)
(Continued)

(52) U.S. Cl.
CPC .............. *G10L 13/02* (2013.01); *G06F 3/165* (2013.01); *G06N 5/02* (2013.01); *G06N 20/00* (2019.01); *G10K 15/08* (2013.01); *G10L 13/033* (2013.01); *G10L 15/02* (2013.01); *G10L 15/063* (2013.01); *G10L 15/065* (2013.01);
(Continued)

(58) Field of Classification Search
CPC ....... G10L 13/02; G10L 13/033; G10L 15/02; G10L 15/063; G10L 15/065; G10L 21/0224; G10L 25/03; G10L 21/02; G10L 21/0208; G10L 25/30; G10L 2021/02082; G06F 3/165; G06N 5/02; G06N 20/00; G06N 3/08; G10K 15/08; G10K 15/02; H04S 7/30; H04S 7/302; H04S 7/303;
(Continued)

(56) References Cited

U.S. PATENT DOCUMENTS 3,983,482 A   9/1976 Doherty
6,490,553 B2  12/2002 Van et al.
(Continued)

OTHER PUBLICATIONS

"Advisory Action Issued in U.S. Appl. No. 17/077,965", Mailed Date: Jul. 13, 2021, 4 Pages.
(Continued)

*Primary Examiner* — Angie Badawi
(74) *Attorney, Agent, or Firm* — Brian J. Colandreo; Heath M. Sargeant; Holland & Knight LLP

(57) ABSTRACT

A method, computer program product, and computing system for generating a three-dimensional model of at least a portion of a three-dimensional space incorporating an ACI system via a video recording subsystem of an ACI calibration platform; and generating one or more audio calibration signals for receipt by an audio recording system included within the ACI system via an audio generation subsystem of the ACI calibration platform.

18 Claims, 10 Drawing Sheets

Related U.S. Application Data

(60) Provisional application No. 62/988,337, filed on Mar. 11, 2020.

(51) Int. Cl.

| | |
|---|---|
| *G06N 5/02* | (2006.01) |
| *G06N 20/00* | (2019.01) |
| *G10K 15/08* | (2006.01) |
| *G10L 13/033* | (2013.01) |
| *G10L 15/02* | (2006.01) |
| *G10L 15/06* | (2013.01) |
| *G10L 15/065* | (2013.01) |
| *G10L 21/0224* | (2013.01) |
| *G10L 25/03* | (2013.01) |
| *H04S 7/00* | (2006.01) |

(52) U.S. Cl.
CPC .......... *G10L 21/0224* (2013.01); *G10L 25/03* (2013.01); *H04S 7/30* (2013.01); *H04S 7/302* (2013.01); *H04S 7/303* (2013.01)

(58) Field of Classification Search
CPC ..... H04S 2400/15; H04S 7/305; H04R 1/406; H04R 3/005
See application file for complete search history.

(56) References Cited

U.S. PATENT DOCUMENTS

| | | |
|---|---|---|
| 6,836,761 B1 | 12/2004 | Kawashima et al. |
| 8,761,410 B1 | 6/2014 | Avendano |
| 8,838,446 B2 | 9/2014 | Jeong et al. |
| 9,008,329 B1 | 4/2015 | Mandel et al. |
| 9,202,464 B1 | 12/2015 | Senior et al. |
| 9,922,664 B2 | 3/2018 | Sharma et al. |
| 10,296,959 B1 | 5/2019 | Chernikhova et al. |
| 10,475,471 B2 | 11/2019 | Ebenezer |
| 10,559,299 B1 | 2/2020 | Arel et al. |
| 10,796,702 B2 | 10/2020 | Li et al. |
| 10,841,424 B1 | 11/2020 | Lemus et al. |
| 11,132,993 B1 | 9/2021 | Mcdaniel et al. |
| 11,361,749 B2 | 6/2022 | Sharma et al. |
| 11,380,312 B1 | 7/2022 | Mansour |
| 11,398,216 B2 | 7/2022 | Sharma et al. |
| 11,482,241 B2 | 10/2022 | Sharma et al. |
| 11,863,948 B1 | 1/2024 | Kwatra et al. |
| 2001/0047267 A1 | 11/2001 | Abiko et al. |
| 2002/0087306 A1 | 7/2002 | Lee et al. |
| 2008/0147413 A1 | 6/2008 | Sobol-Shikler |
| 2008/0188257 A1 | 8/2008 | Mickle et al. |
| 2011/0051948 A1 | 3/2011 | Boldt et al. |
| 2011/0066390 A1 | 3/2011 | Macleod et al. |
| 2011/0103468 A1 | 5/2011 | Polisetty et al. |
| 2013/0073960 A1 | 3/2013 | Eppolito et al. |
| 2013/0151247 A1 | 6/2013 | Lou et al. |
| 2013/0211826 A1 | 8/2013 | Mannby |
| 2014/0294200 A1 | 10/2014 | Baumgarte et al. |
| 2015/0092950 A1 | 4/2015 | Kim et al. |
| 2015/0117652 A1 | 4/2015 | Sato et al. |
| 2015/0195406 A1 | 7/2015 | Dwyer et al. |
| 2015/0332680 A1 | 11/2015 | Crockett et al. |
| 2016/0187654 A1 | 6/2016 | Border et al. |
| 2016/0240210 A1 | 8/2016 | Lou |
| 2017/0330071 A1 | 11/2017 | Roblek et al. |
| 2018/0018590 A1 | 1/2018 | Szeto et al. |
| 2018/0082692 A1 | 3/2018 | Khoury et al. |
| 2018/0146047 A1 | 5/2018 | Biswas et al. |
| 2018/0342258 A1 | 11/2018 | Huffman et al. |
| 2019/0013013 A1 | 1/2019 | Mclaren et al. |
| 2019/0028696 A1 | 1/2019 | Dietz et al. |
| 2019/0035415 A1 | 1/2019 | Lu et al. |
| 2019/0272145 A1 | 9/2019 | Sharma et al. |
| 2019/0272818 A1 | 9/2019 | Fernandez et al. |
| 2019/0272840 A1 | 9/2019 | Caroselli et al. |
| 2019/0362711 A1 | 11/2019 | Nosrati et al. |
| 2020/0050701 A1 | 2/2020 | Ramasamy et al. |
| 2020/0258510 A1 | 8/2020 | Lavery et al. |
| 2020/0275207 A1 | 8/2020 | Zilberman et al. |
| 2020/0285702 A1 | 9/2020 | Padhi et al. |
| 2020/0309930 A1 | 10/2020 | Zhou et al. |
| 2020/0311300 A1 | 10/2020 | Callcut et al. |
| 2020/0335086 A1 | 10/2020 | Paraskevopoulos et al. |
| 2021/0055778 A1 | 2/2021 | Myer et al. |
| 2021/0287105 A1 | 9/2021 | Sharma et al. |
| 2021/0287652 A1 | 9/2021 | Sharma et al. |
| 2021/0287653 A1 | 9/2021 | Sharma et al. |
| 2021/0287654 A1 | 9/2021 | Sharma et al. |
| 2021/0287659 A1 | 9/2021 | Sharma et al. |
| 2021/0287660 A1 | 9/2021 | Sharma et al. |
| 2021/0287661 A1 | 9/2021 | Sharma et al. |
| 2021/0304737 A1 | 9/2021 | Han et al. |
| 2022/0246131 A1 | 8/2022 | Sharma et al. |
| 2022/0270625 A1 | 8/2022 | Dai et al. |
| 2022/0301573 A1 | 9/2022 | Wang et al. |
| 2022/0310055 A1 | 9/2022 | Sharma et al. |

OTHER PUBLICATIONS

"Non Final Office Action Issued in U.S. Appl. No. 17/077,965", Mailed Date: Nov. 9, 2021, 8 Pages.

"Notice of Allowance Issued in U.S. Appl. No. 17/077,965", Mailed Date: May 18, 2022, 6 Pages.

"Notice of Allowance Issued in U.S. Appl. No. 17/077,965", Mailed Date: Feb. 24, 2022, 8 Pages.

"Non Final Office Action Issued in U.S. Appl. No. 17/197,717", Mailed Date: Jul. 14, 2022, 10 Pages.

"Non Final Office Action Issued in U.S. Appl. No. 17/197,549", Mail Date: Sep. 1, 2022, 16 Pages.

"Non Final Office Action Issued in U.S. Appl. No. 17/197,650", Mail Date: Oct. 12, 2022, 19 Pages.

"Non Final Office Action Issued in U.S. Appl. No. 17/728,252", Mail Date: Oct. 12, 2022, 12 Pages.

"Final Office Action Issued in U.S. Appl. No. 17/197,684", Mail Date: May 15, 2023, 16 Pages.

"Non Final Office Action Issued in U.S. Appl. No. 17/197,650", Mail Date: Jun. 30, 2023, 17 Pages.

"Advisory Action Issued in U.S. Appl. No. 17/197,740", Mail Date: Jul. 3, 2023, 6 Pages.

Coleman, et al., "On Object-Based Audio with Reverberation", In Proceedings of the 60th International Conference on Dereverberation and Reverberation of Audio, Music, and Speech, Audio Engineering Society, Feb. 3, 2016, 10 Pages.

"Non Final Office Action Issued in U.S. Appl. No. 17/197,549", Mailed Date: Sep. 6, 2023, 20 Pages.

"Non Final Office Action Issued In U.S. Appl. No. 17/197,684", Mailed Date: Oct. 3, 2023, 19 Pages.

"Non Final Office Action Issued in U.S. Appl. No. 17/197,740", Mail Date: Aug. 7, 2023, 24 Pages.

Kim, et al., "Environmental Noise Embeddings for Robust Speech Recognition", In Repository of arXiv: 1601.02553v2, Sep. 29, 2016, 5 Pages.

Madhu, et al., "Data Augmentation using Generative Adversarial Network for Environmental Sound Classification", In Proceedings of the 27th European Signal Processing Conference, Sep. 2, 2019, 5 Pages.

Mathur, et al., "Mic2mic: Using Cycle-Consistent Generative Adversarial Networks to Overcome Microphone Variability in Speech Systems", In Proceedings of the 18th International Conference on Information Processing in Sensor Networks, Apr. 16, 2019, pp. 169-180.

Nagano, et al., "Data Augmentation Based on Vowel Stretch for Improving Children's Speech Recognition", In Proceedings of the IEEE Automatic Speech Recognition and Understanding Workshop, Dec. 14, 2019, pp. 502-508.

"Advisory Action Issued in U.S. Appl. No. 17/197,587", Mail Date: Feb. 28, 2023, 5 Pages.

"Non Final Office Action Issued in U.S. Appl. No. 17/197,587", Mail Date: Mar. 30, 2023, 21 Pages.

(56) References Cited

OTHER PUBLICATIONS

"Final Office Action Issued in U.S. Appl. No. 17/197,740", Mail Date: Mar. 9, 2023, 22 Pages.
Mathur, et al., "Using Deep Data Augmentation Training to Address Software and Hardware Heterogeneities in Wearable and Smartphone Sensing Devices", In Proceedings of 17th ACM/IEEE International Conference on Information Processing in Sensor Networks, Apr. 11, 2018, pp. 200-211.
Sun, et al., "An Unsupervised Deep Domain Adaptation Approach for Robust Speech Recognition", In Journal of Neurocomputing, vol. 257, Sep. 27, 2017, pp. 79-87.
"Final Office Action Issued in U.S. Appl. No. 17/197,650", Mail Date: Feb. 24, 2023, 15 Pages.
"Final Office Action Issued in U.S. Appl. No. 17/197,549", Mail Date: Feb. 7, 2023, 18 Pages.
"Final Office Action Issued in U.S. Appl. No. 17/197,717", Mail Date: Jan. 20, 2023, 15 Pages.
"Notice of Allowance Issued in U.S. Appl. No. 17/728,252", Mail Date: Jan. 25, 2023, 9 Pages.
"Final Office Action Issued in U.S. Appl. No. 17/197,587", Mail Date: Dec. 6, 2022, 20 Pages.
"Non Final Office Action Issued in U.S. Appl. No. 17/197,684", Mail Date: Nov. 28, 2022, 14 Pages.
"Non Final Office Action Issued in U.S. Appl. No. 17/197,740", Mail Date: Nov. 14, 2022, 23 Pages.
Hsu, et al., "Unsupervised Domain Adaptation for Robust Speech Recognition via Variational Autoencoder-based Data Augmentation", In Proceedings of IEEE Automatic Speech Recognition and Understanding Workshop, Dec. 16, 2017, pp. 16-23.
Mazalov, et al., "Microsoft Cognitive Toolkit (CNTK), An Open Source Deep-Learning Toolkit", Retrieved From: https://web.archive.org/web/20190112114726/https://github.com/microsoft/CNTK, Jan. 12, 2019, 10 Pages.
Nishizaki, Hiromitsu, "Data Augmentation and Feature Extraction using Variational Autoencoder for Acoustic Modeling", In Proceedings of Asia-Pacific Signal and Information Processing Association Annual Summit and Conference, Dec. 12, 2017, 6 Pages.
Salamon, et al., "Deep Convolutional Neural Networks and Data Augmentation for Environmental Sound Classification", In Journal of IEEE Signal Processing Letters, vol. 24, Issue 3, Mar. 2017, pp. 279-283.
"Final Office Action Issued in U.S. Appl. No. 17/197,740", Mail Date: Nov. 22, 2023, 25 Pages.
"Final Office Action Issued in U.S. Appl. No. 17/197,587", Mail Date: Oct. 13, 2023, 23 Pages.
"Notice of Allowance Issued in U.S. Appl. No. 17/197,650", Mail Date: Oct. 23, 2023, 10 Pages.
Non-Final Office Action mailed on Dec. 14, 2023, in U.S. Appl. No. 17/197,717, 21 pages.
Notice of Allowance mailed on Dec. 18, 2023, in U.S. Appl. No. 17/197,650, 4 pages.
Supplementary European Search Report Recieved for European Application No. 21766972.0, mailed on Mar. 4, 2024, 8 pages.
Airaksinen, et al., "Data Augmentation Strategies for Neural Network F0 Estimation," ICASSP 2019—2019 IEEE International Conference on Acoustics, Speech and Signal Processing (ICASSP), Brighton, UK, 2019, pp. 6485-6489.
Final Office Action mailed on Feb. 6, 2024, in U.S. Appl. No. 17/197,549, 22 Pages.
Final Office Action mailed on Feb. 16, 2024, in U.S. Appl. No. 17/197,684, 21 pages.
Notice of Allowance mailed on Feb. 6, 2024, in U.S. Appl. No. 17/197,587, 14 Pages.
Szoke, et al., "Building and evaluation of a real room impulse response dataset", IEEE Journal of Selected Topics in Signal Processing, vol. 13 No. 4, Aug. 2019, pp. 863-876.

AMBIENT COOPERATIVE INTELLIGENCE SYSTEM AND METHOD

RELATED APPLICATION(S)

This application is a continuation of Non-Provisional application Ser. No. 17/077,863, filed 22 Oct. 2020, which claims the benefit of U.S. Provisional Application No. 62/988,337, filed on 11 Mar. 2020, the entire contents of which are herein incorporated by reference.

TECHNICAL FIELD

This disclosure relates to intelligence systems and methods and, more particularly, to ambient cooperative intelligence systems and methods.

BACKGROUND

As is known in the art, cooperative intelligence is the creation of reports and documentation that details the history of an event/individual. As would be expected, traditional documentation includes various types of data, examples of which may include but are not limited to paper-based documents and transcripts, as well as various images and diagrams.

As the world moved from paper-based content to digital content, traditional documentation also moved in that direction, where reports and documentation were gradually transitioned from stacks of paper geographically-dispersed across multiple locations/institutions to consolidated and readily accessible digital content.

SUMMARY OF DISCLOSURE

In one implementation, a computer-implemented method is executed on a computing device and includes: generating a three-dimensional model of at least a portion of a three-dimensional space incorporating an ACI system via a video recording subsystem of an ACI calibration platform; and generating one or more audio calibration signals for receipt by an audio recording system included within the ACI system via an audio generation subsystem of the ACI calibration platform.

One or more of the following features may be included. The ACI calibration platform may be autonomously positioned within the three-dimensional space via a mobile base assembly of the ACI calibration platform. At least a portion of the three-dimensional space may be autonomously cleaned via a cleaning assembly of the ACI calibration platform. The ACI calibration platform may be configured to be manually positioned within the three-dimensional space. The video recording system of the ACI calibration platform may be configured to interface with an object datasource that defines a plurality of objects that may be located within the three-dimensional space. The three-dimensional model may be configured to define at least one of: one or more subspaces within the three-dimensional space; one or more objects within the three-dimensional space; one or more features within the three-dimensional space; one or more interaction zones within the three-dimensional space; and one or more noise sources within the three-dimensional space. The one or more audio calibration signals may include one or more of: a noise signal; a sinusoid signal; and a multi-frequency signal.

In another implementation, a computer program product resides on a computer readable medium and has a plurality of instructions stored on it. When executed by a processor, the instructions cause the processor to perform operations including: generating a three-dimensional model of at least a portion of a three-dimensional space incorporating an ACI system via a video recording subsystem of an ACI calibration platform; and generating one or more audio calibration signals for receipt by an audio recording system included within the ACI system via an audio generation subsystem of the ACI calibration platform.

One or more of the following features may be included. The ACI calibration platform may be autonomously positioned within the three-dimensional space via a mobile base assembly of the ACI calibration platform. At least a portion of the three-dimensional space may be autonomously cleaned via a cleaning assembly of the ACI calibration platform. The ACI calibration platform may be configured to be manually positioned within the three-dimensional space. The video recording system of the ACI calibration platform may be configured to interface with an object datasource that defines a plurality of objects that may be located within the three-dimensional space. The three-dimensional model may be configured to define at least one of: one or more subspaces within the three-dimensional space; one or more objects within the three-dimensional space; one or more features within the three-dimensional space; one or more interaction zones within the three-dimensional space; and one or more noise sources within the three-dimensional space. The one or more audio calibration signals may include one or more of: a noise signal; a sinusoid signal; and a multi-frequency signal.

In another implementation, a computing system includes a processor and memory is configured to perform operations including: generating a three-dimensional model of at least a portion of a three-dimensional space incorporating an ACI system via a video recording subsystem of an ACI calibration platform; and generating one or more audio calibration signals for receipt by an audio recording system included within the ACI system via an audio generation subsystem of the ACI calibration platform.

One or more of the following features may be included. The ACI calibration platform may be autonomously positioned within the three-dimensional space via a mobile base assembly of the ACI calibration platform. At least a portion of the three-dimensional space may be autonomously cleaned via a cleaning assembly of the ACI calibration platform. The ACI calibration platform may be configured to be manually positioned within the three-dimensional space. The video recording system of the ACI calibration platform may be configured to interface with an object datasource that defines a plurality of objects that may be located within the three-dimensional space. The three-dimensional model may be configured to define at least one of: one or more subspaces within the three-dimensional space; one or more objects within the three-dimensional space; one or more features within the three-dimensional space; one or more interaction zones within the three-dimensional space; and one or more noise sources within the three-dimensional space. The one or more audio calibration signals may include one or more of: a noise signal; a sinusoid signal; and a multi-frequency signal.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
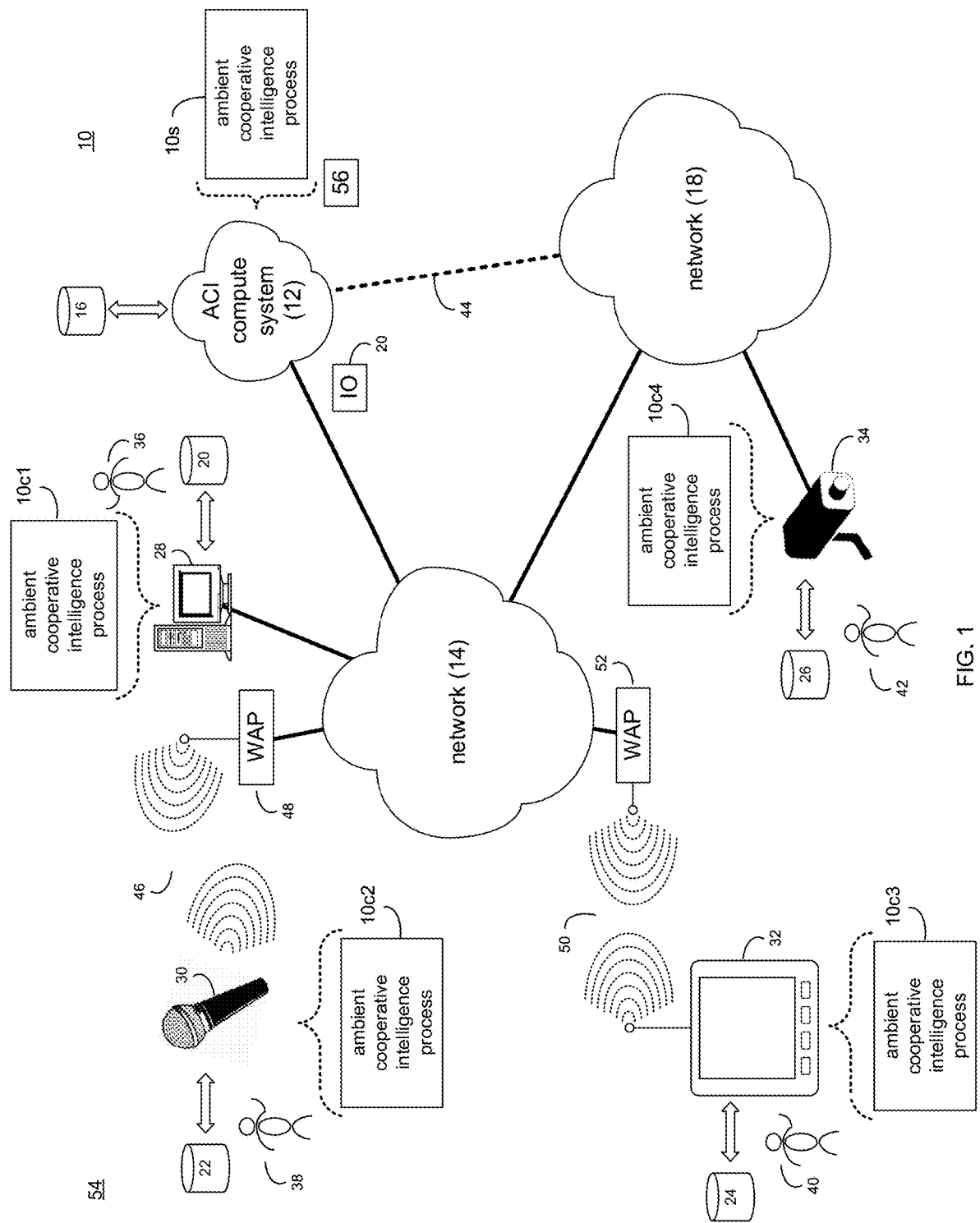
FIG. 1 is a diagrammatic view of an ambient cooperative intelligence compute system and an ambient cooperative intelligence process coupled to a distributed computing network.

Referring to FIG. 1, there is shown ambient cooperative intelligence process 10. As will be discussed below in greater detail, ambient cooperative intelligence process 10 may be configured to automate the collection and processing of encounter information to generate/store/distribute reports.

Ambient cooperative intelligence process 10 may be implemented as a server-side process, a client-side process, or a hybrid server-side/client-side process. For example, ambient cooperative intelligence process 10 may be implemented as a purely server-side process via ambient cooperative intelligence process 10s. Alternatively, ambient cooperative intelligence process 10 may be implemented as a purely client-side process via one or more of ambient cooperative intelligence process 10c1, ambient cooperative intelligence process 10c2, ambient cooperative intelligence process 10c3, and ambient cooperative intelligence process 10c4. Alternatively still, ambient cooperative intelligence process 10 may be implemented as a hybrid server-side/client-side process via ambient cooperative intelligence process 10s in combination with one or more of ambient cooperative intelligence process 10c1, ambient cooperative intelligence process 10c2, ambient cooperative intelligence process 10c3, and ambient cooperative intelligence process 10c4.

Accordingly, ambient cooperative intelligence process 10 as used in this disclosure may include any combination of ambient cooperative intelligence process 10s, ambient cooperative intelligence process 10c1, ambient cooperative intelligence process 10c2, ambient cooperative intelligence process 10c3, and ambient cooperative intelligence process 10c4.

Ambient cooperative intelligence process 10s may be a server application and may reside on and may be executed by ambient cooperative intelligence (ACI) compute system 12, which may be connected to network 14 (e.g., the Internet or a local area network). ACI compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACI compute system 12 may execute one or more operating systems, examples of which may include but are not limited to: Microsoft Windows Server™; Redhat Linux™, Unix, or a custom operating system, for example.

The instruction sets and subroutines of ambient cooperative intelligence process 10s, which may be stored on storage device 16 coupled to ACI compute system 12, may be executed by one or more processors (not shown) and one or more memory architectures (not shown) included within ACI compute system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from ambient cooperative intelligence process 10s, ambient cooperative intelligence process 10c1, ambient cooperative intelligence process 10c2, ambient cooperative intelligence process 10c3 and/or ambient cooperative intelligence process 10c4 to ACI compute system 12. Examples of IO request 20 may include but are not limited to data write requests (i.e. a request that content be written to ACI compute system 12) and data read requests (i.e. a request that content be read from ACI compute system 12).

The instruction sets and subroutines of ambient cooperative intelligence process 10c1, ambient cooperative intelligence process 10c2, ambient cooperative intelligence process 10c3 and/or ambient cooperative intelligence process 10c4, which may be stored on storage devices 20, 22, 24, 26 (respectively) coupled to ACI client electronic devices 28, 30, 32, 34 (respectively), may be executed by one or more processors (not shown) and one or more memory architectures (not shown) incorporated into ACI client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACI client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACI compute system 12 directly through network 14 or through secondary network 18. Further, ACI compute system 12 may be connected to network 14 through secondary network 18, as illustrated with link line 44.

The various ACI client electronic devices (e.g., ACI client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACI client electronic devices (e.g., ACI client electronic devices 28, 30, 32, 34) may each execute an operating system, examples of which may include but are not limited to Microsoft Windows™, Apple Macintosh™, Redhat Linux™, or a custom operating system, wherein the combination of the various ACI client electronic devices (e.g., ACI client electronic devices 28, 30, 32, 34) and ACI compute system 12 may form modular ACI system 54.

The Ambient Cooperative Intelligence System

While ambient cooperative intelligence process 10 will be described below as being utilized to automate the collection and processing of clinical encounter information to generate/store/distribute medical records, this is for illustrative purposes only and is not intended to be a limitation of this disclosure, as other configurations are possible and are considered to be within the scope of this disclosure.

Figure 2:
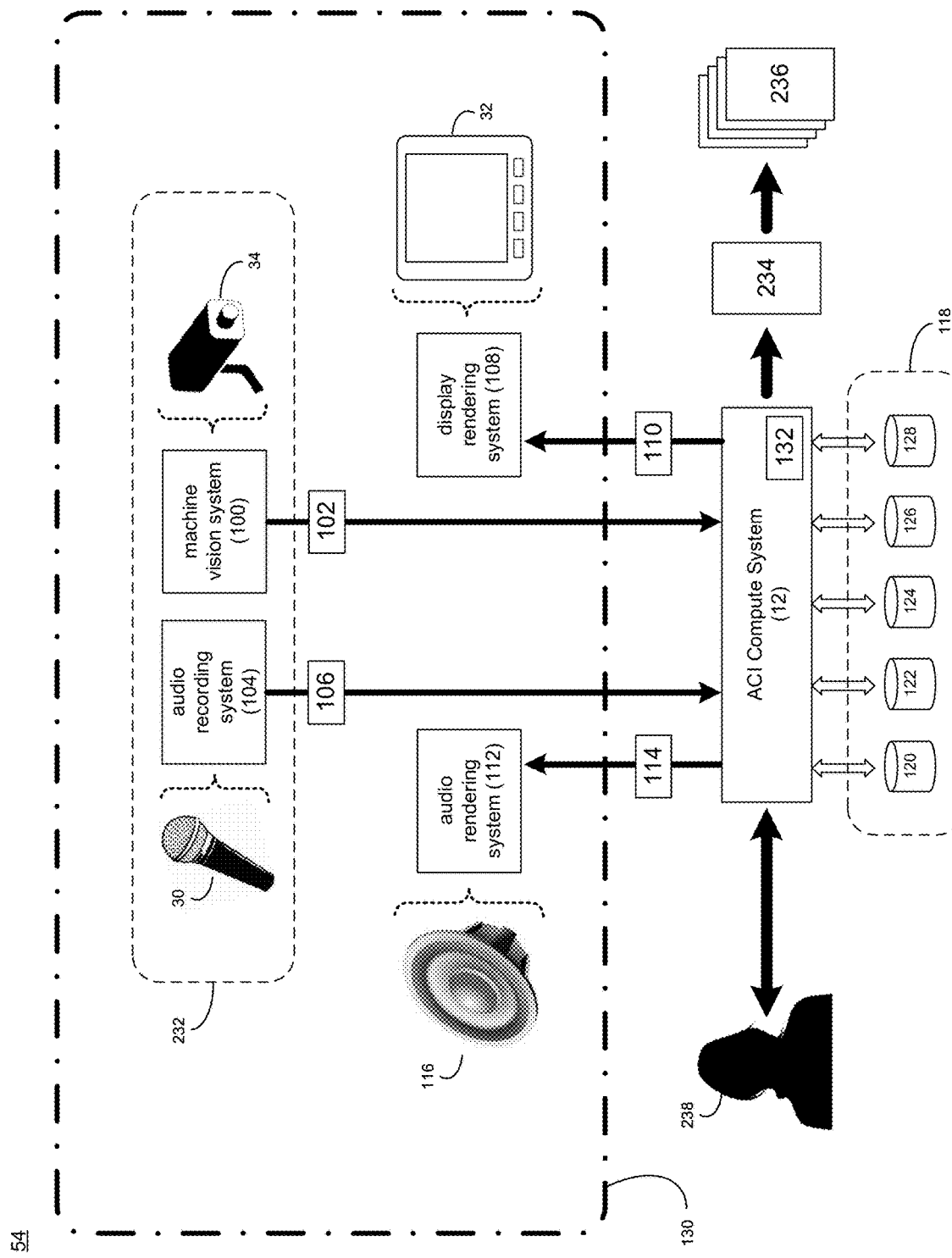
FIG. 2 is a diagrammatic view of a modular ACI system incorporating the ambient cooperative intelligence compute system of FIG. 1.

Referring also to FIG. 2, there is shown a simplified exemplary embodiment of modular ACI system 54 that is configured to automate cooperative intelligence. Modular ACI system 54 may include: machine vision system 100 configured to obtain machine vision encounter information 102 concerning a patient encounter; audio recording system 104 configured to obtain audio encounter information 106 concerning the patient encounter; and a compute system (e.g., ACI compute system 12) configured to receive machine vision encounter information 102 and audio encounter information 106 from machine vision system 100 and audio recording system 104 (respectively). Modular ACI system 54 may also include: display rendering system 108 configured to render visual information 110; and audio rendering system 112 configured to render audio information 114, wherein ACI compute system 12 may be configured to provide visual information 110 and audio information 114 to display rendering system 108 and audio rendering system 112 (respectively).

Example of machine vision system 100 may include but are not limited to: one or more ACI client electronic devices (e.g., ACI client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACI client electronic devices (e.g., ACI client electronic device 30, examples of which may include but are not limited to a handheld microphone (e.g., one example of a body worn microphone), a lapel microphone (e.g., another example of a body worn microphone), an embedded microphone, such as those embedded within eyeglasses, smart phones, tablet computers and/or watches (e.g., another example of a body worn microphone), and an audio recording device). Examples of display rendering system 108 may include but are not limited to: one or more ACI client electronic devices (e.g., ACI client electronic device 32, examples of which may include but are not limited to a tablet computer, a computer monitor, and a smart television). Examples of audio rendering system 112 may include but are not limited to: one or more ACI client electronic devices (e.g., audio rendering device 116, examples of which may include but are not limited to a speaker system, a headphone system, and an earbud system).

ACI compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the ambient speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource. While in this particular example, five different examples of datasources 118 are shown, this is for illustrative purposes only and is not intended to be a limitation of this disclosure, as other configurations are possible and are considered to be within the scope of this disclosure.

As will be discussed below in greater detail, modular ACI system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACI client electronic devices (e.g., ACI client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACI client electronic devices (e.g., ACI client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACI client electronic devices (e.g., ACI client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACI client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACI compute system 12 may include a plurality of discrete compute systems. As discussed above, ACI compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACI compute system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Microphone Array

Figure 3:
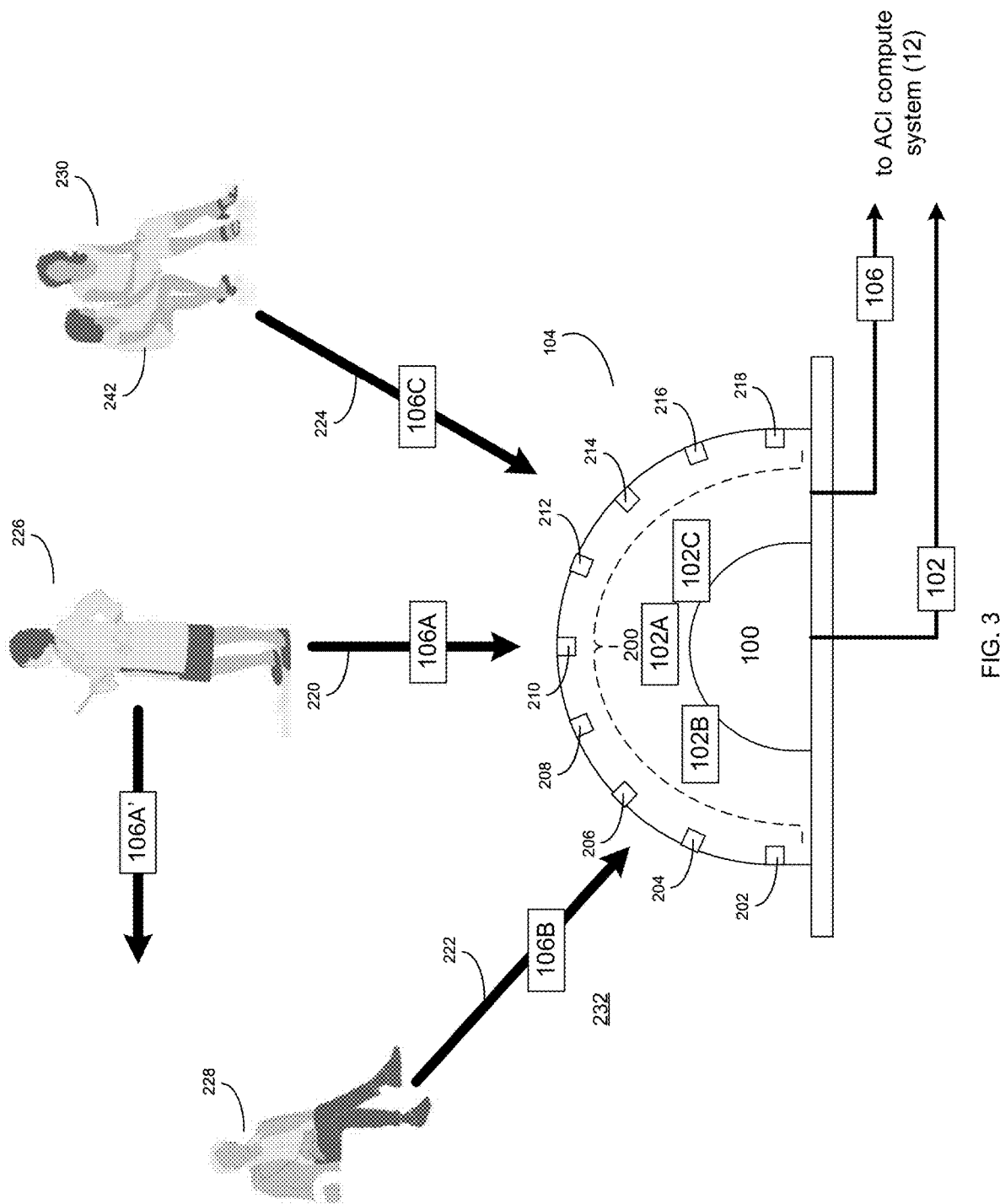
FIG. 3 is a diagrammatic view of a mixed-media ACI device included within the modular ACI system of FIG. 2.

Referring also to FIG. 3, audio recording system 104 may include microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACI system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACI system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACI system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACI system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACI system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230).

Further, modular ACI system 54 and/or audio recording system 104 may be configured to utilize null-steering precoding to cancel interference between speakers and/or noise. As is known in the art, null-steering precoding is a method of spatial signal processing by which a multiple antenna transmitter may null multiuser interference signals in wireless communications, wherein null-steering precoding may mitigate the impact off background noise and unknown user interference. In particular, null-steering precoding may be a method of beamforming for narrowband signals that may compensate for delays of receiving signals from a specific source at different elements of an antenna array. In general and to improve performance of the antenna array, incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACI device 232. For example, mixed-media ACI device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACI system 54 may be configured to include a plurality of mixed-media ACI devices (e.g., mixed-media ACI device 232) when the above-described clinical environment is larger or a higher level of resolution is desired.

Modular ACI system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACI device 232 (and machine vision system 100/audio recording system 104 included therein) may be configured to monitor one or more encounter participants (e.g., encounter participants 226, 228, 230) of a patient encounter.

Specifically and as will be discussed below in greater detail, machine vision system 100 (either as a stand-alone system or as a component of mixed-media ACI device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACI compute system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACI system 54 (and/or mixed-media ACI device 232) is configured, ACI compute system 12 may be included within mixed-media ACI device 232 or external to mixed-media ACI device 232. The Ambient Cooperative Intelligence Process As discussed above, ACI compute system 12 may execute all or a portion of ambient cooperative intelligence process 10, wherein the instruction sets and subroutines of ambient cooperative intelligence process 10 (which may be stored on one or more of e.g., storage devices 16, 20, 22, 24, 26) may be executed by ACI compute system 12 and/or one or more of ACI client electronic devices 28, 30, 32, 34.

Figure 4:
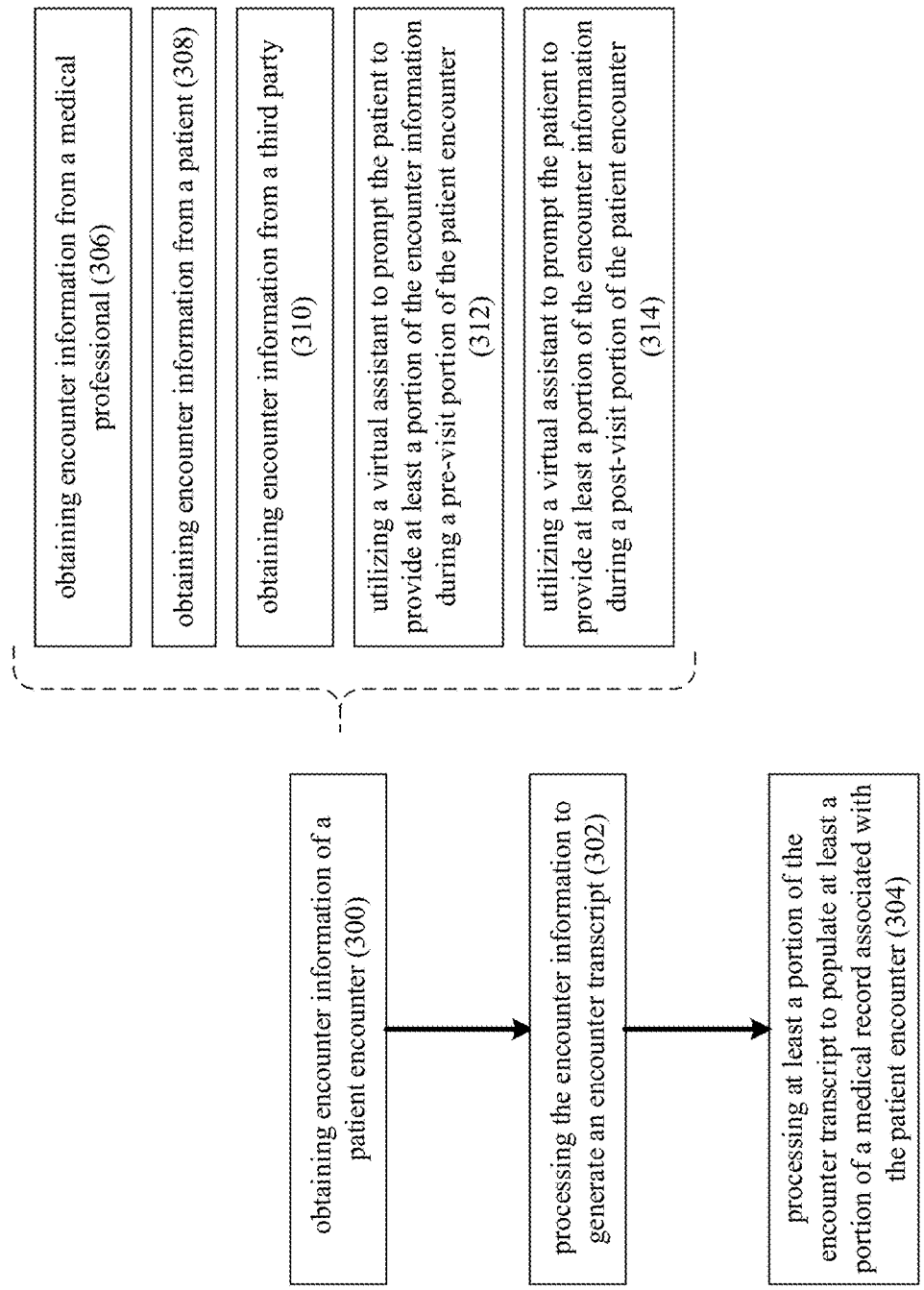
FIG. 4 is a flow chart of one implementation of the ambient cooperative intelligence process of FIG. 1.

As discussed above, ambient cooperative intelligence process 10 may be configured to automate the collection and processing of clinical encounter information to generate/store/distribute medical records. Accordingly and referring also to FIG. 4, ambient cooperative intelligence process 10 may be configured to obtain 300 encounter information (e.g., machine vision encounter information 102 and/or audio encounter information 106) of a patient encounter (e.g., a visit to a doctor's office). Ambient cooperative intelligence process 10 may further be configured to process 302 the encounter information (e.g., machine vision encounter information 102 and/or audio encounter information 106) to generate an encounter transcript (e.g., encounter transcript 234), wherein ambient cooperative intelligence process 10 may then process 304 at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, ambient cooperative intelligence process 10 may utilize these corrections for training/tuning purposes (e.g., to adjust the various profiles associated the participants of the patient encounter) to enhance the future accuracy/efficiency/performance of ambient cooperative intelligence process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, ambient cooperative intelligence process 10 may utilize these corrections for training/tuning purposes (e.g., to adjust the various profiles associated the participants of the patient encounter) to enhance the future accuracy/efficiency/performance of ambient cooperative intelligence process 10.

For example, assume that a patient (e.g., encounter participant 228) visits a clinical environment (e.g., a doctor's office) because they do not feel well. They have a headache, fever, chills, a cough, and some difficulty breathing. In this particular example, a monitored space (e.g., monitored space 130) within the clinical environment (e.g., the doctor's office) may be outfitted with machine vision system 100 configured to obtain machine vision encounter information 102 concerning the patient encounter (e.g., encounter participant 228 visiting the doctor's office) and audio recording system 104 configured to obtain audio encounter information 106 concerning the patient encounter (e.g., encounter participant 228 visiting the doctor's office) via one or more audio sensors (e.g., audio acquisition devices 202, 204, 206, 208, 210, 212, 214, 216, 218).

As discussed above, machine vision system 100 may include a plurality of discrete machine vision systems if the monitored space (e.g., monitored space 130) within the clinical environment (e.g., the doctor's office) is larger or a higher level of resolution is desired, wherein examples of machine vision system 100 may include but are not limited to: an RGB imaging system, an infrared imaging system, an ultraviolet imaging system, a laser imaging system, a SONAR imaging system, a RADAR imaging system, and a thermal imaging system. Accordingly and in certain instances/embodiments, machine vision system 100 may include one or more of each of an RGB imaging system, an infrared imaging system, an ultraviolet imaging system, a laser imaging system, a SONAR imaging system, a RADAR imaging system, and a thermal imaging system positioned throughout monitored space 130, wherein each of these systems may be configured to provide data (e.g., machine vision encounter information 102) to ACI compute system 12 and/or modular ACI system 54.

As also discussed above, audio recording system 104 may include a plurality of discrete audio recording systems if the monitored space (e.g., monitored space 130) within the clinical environment (e.g., the doctor's office) is larger or a higher level of resolution is desired, wherein examples of audio recording system 104 may include but are not limited to: a handheld microphone, a lapel microphone, an embedded microphone (such as those embedded within eyeglasses, smart phones, tablet computers and/or watches) and an audio recording device. Accordingly and in certain instances/embodiments, audio recording system 104 may include one or more of each of a handheld microphone, a lapel microphone, an embedded microphone (such as those embedded within eyeglasses, smart phones, tablet computers and/or watches) and an audio recording device positioned throughout monitored space 130, wherein each of these microphones/devices may be configured to provide data (e.g., audio encounter information 106) to ACI compute system 12 and/or modular ACI system 54.

Since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and via machine vision encounter information 102, visual speech recognition (via visual lip reading functionality) may be utilized by ambient cooperative intelligence process 10 to further effectuate the gathering of audio encounter information 106.

Accordingly and when obtaining 300 encounter information (e.g., machine vision encounter information 102 and/or audio encounter information 106), ambient cooperative intelligence process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), ambient cooperative intelligence process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by ambient cooperative intelligence process 10.

When ambient cooperative intelligence process 10 obtains 300 the encounter information, ambient cooperative intelligence process 10 may utilize 312 a virtual assistant (e.g., virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office).

Further and when ambient cooperative intelligence process 10 obtains 300 encounter information, ambient cooperative intelligence process 10 may utilize 314 a virtual assistant (e.g., virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office).

Automated Transcript Generation

Ambient cooperative intelligence process 10 may be configured to process the encounter information (e.g., machine vision encounter information 102 and/or audio encounter information 106) to generate encounter transcript 234 that may be automatically formatted and punctuated.

Figure 5:
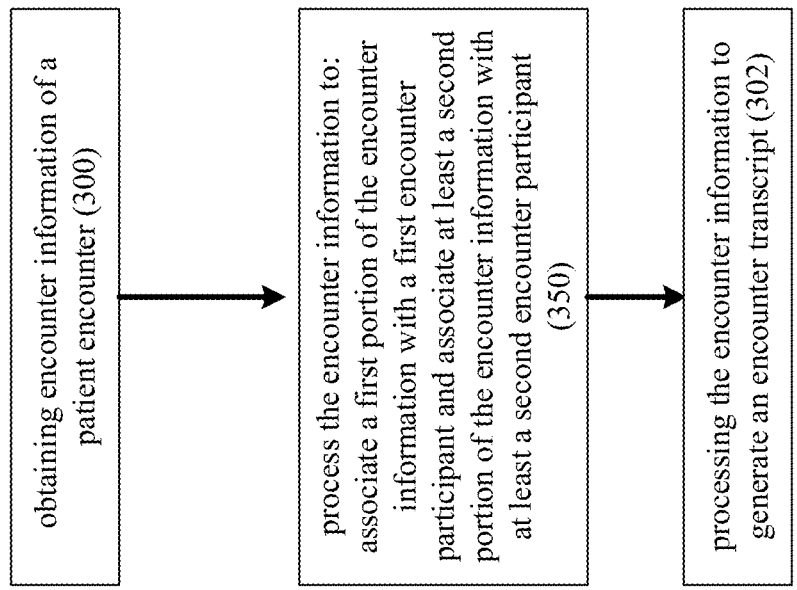
FIG. 5 is a flow chart of another implementation of the ambient cooperative intelligence process of FIG. 1.

Accordingly and referring also to FIG. 5, ambient cooperative intelligence process 10 may be configured to obtain 300 encounter information (e.g., machine vision encounter information 102 and/or audio encounter information 106) of a patient encounter (e.g., a visit to a doctor's office).

Ambient cooperative intelligence process 10 may process 350 the encounter information (e.g., machine vision encounter information 102 and/or audio encounter information 106) to: associate a first portion of the encounter information (e.g., machine vision encounter information 102 and/or audio encounter information 106) with a first encounter participant, and associate at least a second portion of the encounter information (e.g., machine vision encounter information 102 and/or audio encounter information 106) with at least a second encounter participant.

As discussed above, modular ACI system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein modular ACI system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, modular ACI system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACI compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource.

Accordingly, ambient cooperative intelligence process 10 may process 350 the encounter information (e.g., machine vision encounter information 102 and/or audio encounter information 106) to: associate a first portion (e.g., encounter information 106A) of the encounter information (e.g., audio encounter information 106) with a first encounter participant (e.g., encounter participant 226), and associate at least a second portion (e.g., encounter information 106B, 106C) of the encounter information (e.g., audio encounter information 106) with at least a second encounter participant (e.g., encounter participants 228, 230; respectively).

Further and when processing 350 the encounter information (e.g., audio encounter information 106A, 106B, 106C), ambient cooperative intelligence process 10 may compare each of audio encounter information 106A, 106B, 106C to the voice prints defined within the above-referenced voice print datasource so that the identity of encounter participants 226, 228, 230 (respectively) may be determined. Accordingly, if the voice print datasource includes a voice print that corresponds to one or more of the voice of encounter participant 226 (as heard within audio encounter information 106A), the voice of encounter participant 228 (as heard within audio encounter information 106B) or the voice of encounter participant 230 (as heard within audio encounter information 106C), the identity of one or more of encounter participants 226, 228, 230 may be defined. And in the event that a voice heard within one or more of audio encounter information 106A, audio encounter information 106B or audio encounter information 106C is unidentifiable, that one or more particular encounter participant may be defined as "Unknown Participant".

Once the voices of encounter participants 226, 228, 230 are processed 350, ambient cooperative intelligence process 10 may generate 302 an encounter transcript (e.g., encounter transcript 234) based, at least in part, upon the first portion of the encounter information (e.g., audio encounter information 106A) and the at least a second portion of the encounter information (e.g., audio encounter information 106B, 106C).

Automated Role Assignment

Ambient cooperative intelligence process 10 may be configured to automatically define roles for the encounter participants (e.g., encounter participants 226, 228, 230) in the patient encounter (e.g., a visit to a doctor's office).

Figure 6:
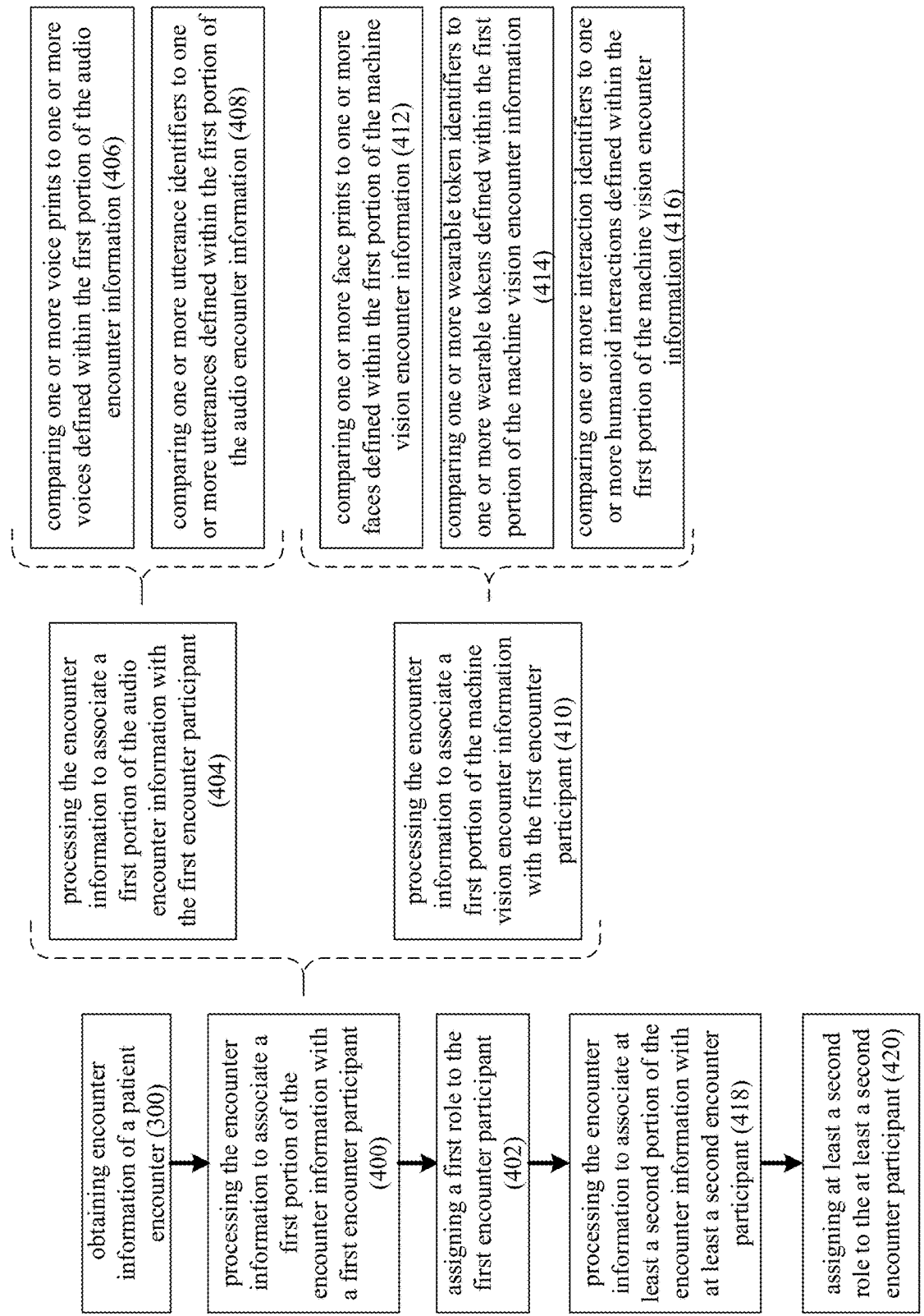
FIG. 6 is a flow chart of another implementation of the ambient cooperative intelligence process of FIG. 1.

Accordingly and referring also to FIG. 6, ambient cooperative intelligence process 10 may be configured to obtain 300 encounter information (e.g., machine vision encounter information 102 and/or audio encounter information 106) of a patient encounter (e.g., a visit to a doctor's office).

Ambient cooperative intelligence process 10 may then process 400 the encounter information (e.g., machine vision encounter information 102 and/or audio encounter information 106) to associate a first portion of the encounter information with a first encounter participant (e.g., encounter participant 226) and assign 402 a first role to the first encounter participant (e.g., encounter participant 226).

When processing 400 the encounter information (e.g., machine vision encounter information 102 and/or audio encounter information 106) to associate the first portion of the encounter information with the first encounter participant (e.g., encounter participant 226), ambient cooperative intelligence process 10 may process 404 the encounter information (e.g., machine vision encounter information 102 and/or audio encounter information 106) to associate a first portion of the audio encounter information (e.g., audio encounter information 106A) with the first encounter participant (e.g., encounter participant 226).

Specifically and when processing 404 the encounter information (e.g., machine vision encounter information 102 and/or audio encounter information 106) to associate the first portion of the audio encounter information (e.g., audio encounter information 106A) with the first encounter participant (e.g., encounter participant 226), ambient cooperative intelligence process 10 may compare 406 one or more voice prints (defined within voice print datasource) to one or more voices defined within the first portion of the audio encounter information (e.g., audio encounter information 106A); and may compare 408 one or more utterance identifiers (defined within utterance datasource) to one or more utterances defined within the first portion of the audio encounter information (e.g., audio encounter information 106A); wherein comparisons 406, 408 may allow ambient cooperative intelligence process 10 to assign 402 a first role to the first encounter participant (e.g., encounter participant 226). For example, if the identity of encounter participant 226 can be defined via voice prints, a role for encounter participant 226 may be assigned 402 if that identity defined is associated with a role (e.g., the identity defined for encounter participant 226 is Doctor Susan Jones). Further, if an utterance made by encounter participant 226 is "I am Doctor Susan Jones", this utterance may allow a role for encounter participant 226 to be assigned 402.

When processing 400 the encounter information (e.g., machine vision encounter information 102 and/or audio encounter information 106) to associate the first portion of the encounter information with the first encounter participant (e.g., encounter participant 226), ambient cooperative intelligence process 10 may process 410 the encounter information (e.g., machine vision encounter information 102 and/or audio encounter information 106) to associate a first portion of the machine vision encounter information (e.g., machine vision encounter information 102A) with the first encounter participant (e.g., encounter participant 226).

Specifically and when processing 410 the encounter information (e.g., machine vision encounter information 102 and/or audio encounter information 106) to associate the first portion of the machine vision encounter information (e.g., machine vision encounter information 102A) with the first encounter participant (e.g., encounter participant 226), ambient cooperative intelligence process 10 may compare 412 one or more face prints (defined within face print datasource) to one or more faces defined within the first portion of the machine vision encounter information (e.g., machine vision encounter information 102A); compare 414 one or more wearable token identifiers (defined within wearable token identifier datasource) to one or more wearable tokens defined within the first portion of the machine vision encounter information (e.g., machine vision encounter information 102A); and compare 416 one or more interaction identifiers (defined within interaction identifier datasource) to one or more humanoid interactions defined within the first portion of the machine vision encounter information (e.g., machine vision encounter information 102A); wherein comparisons 412, 414, 416 may allow ambient cooperative intelligence process 10 to assign 402 a first role to the first encounter participant (e.g., encounter participant 226). For example, if the identity of encounter participant 226 can be defined via face prints, a role for encounter participant 226 may be assigned 402 if that identity defined is associated with a role (e.g., the identity defined for encounter participant 226 is Doctor Susan Jones). Further, if a wearable token worn by encounter participant 226 can be identified as a wearable token assigned to Doctor Susan Jones, a role for encounter participant 226 may be assigned 402. Additionally, if an interaction made by encounter participant 226 corresponds to the type of interaction that is made by a doctor, the existence of this interaction may allow a role for encounter participant 226 to be assigned 402.

Examples of such wearable tokens may include but are not limited to wearable devices that may be worn by the medical professionals when they are within monitored space 130 (or after they leave monitored space 130). For example, these wearable tokens may be worn by medical professionals when e.g., they are moving between monitored rooms within monitored space 130, travelling to and/or from monitored space 130, and/or outside of monitored space 130 (e.g., at home).

Additionally, ambient cooperative intelligence process 10 may process 418 the encounter information (e.g., machine vision encounter information 102 and/or audio encounter information 106) to associate at least a second portion of the encounter information with at least a second encounter participant; and may assign 420 at least a second role to the at least a second encounter participant.

Specifically, ambient cooperative intelligence process 10 may process 418 the encounter information (e.g., machine vision encounter information 102 and/or audio encounter information 106) to associate at least a second portion of the encounter information with at least a second encounter participant. For example, ambient cooperative intelligence process 10 may process 418 the encounter information (e.g., machine vision encounter information 102 and/or audio encounter information 106) to associate audio encounter information 106B and machine vision encounter information 102B with encounter participant 228 and may associate audio encounter information 106C and machine vision encounter information 102C with encounter participant 230.

Further, ambient cooperative intelligence process 10 may assign 420 at least a second role to the at least a second encounter participant. For example, ambient cooperative intelligence process 10 may assign 420 a role to encounter participants 228, 230.

Automated Movement Tracking

Ambient cooperative intelligence process 10 may be configured to track the movement and/or interaction of humanoid shapes within the monitored space (e.g., monitored space 130) during the patient encounter (e.g., a visit to a doctor's office) so that e.g., the ambient cooperative intelligence process 10 knows when encounter participants (e.g., one or more of encounter participants 226, 228, 230) enter, exit or cross paths within monitored space 130.

Figure 7:
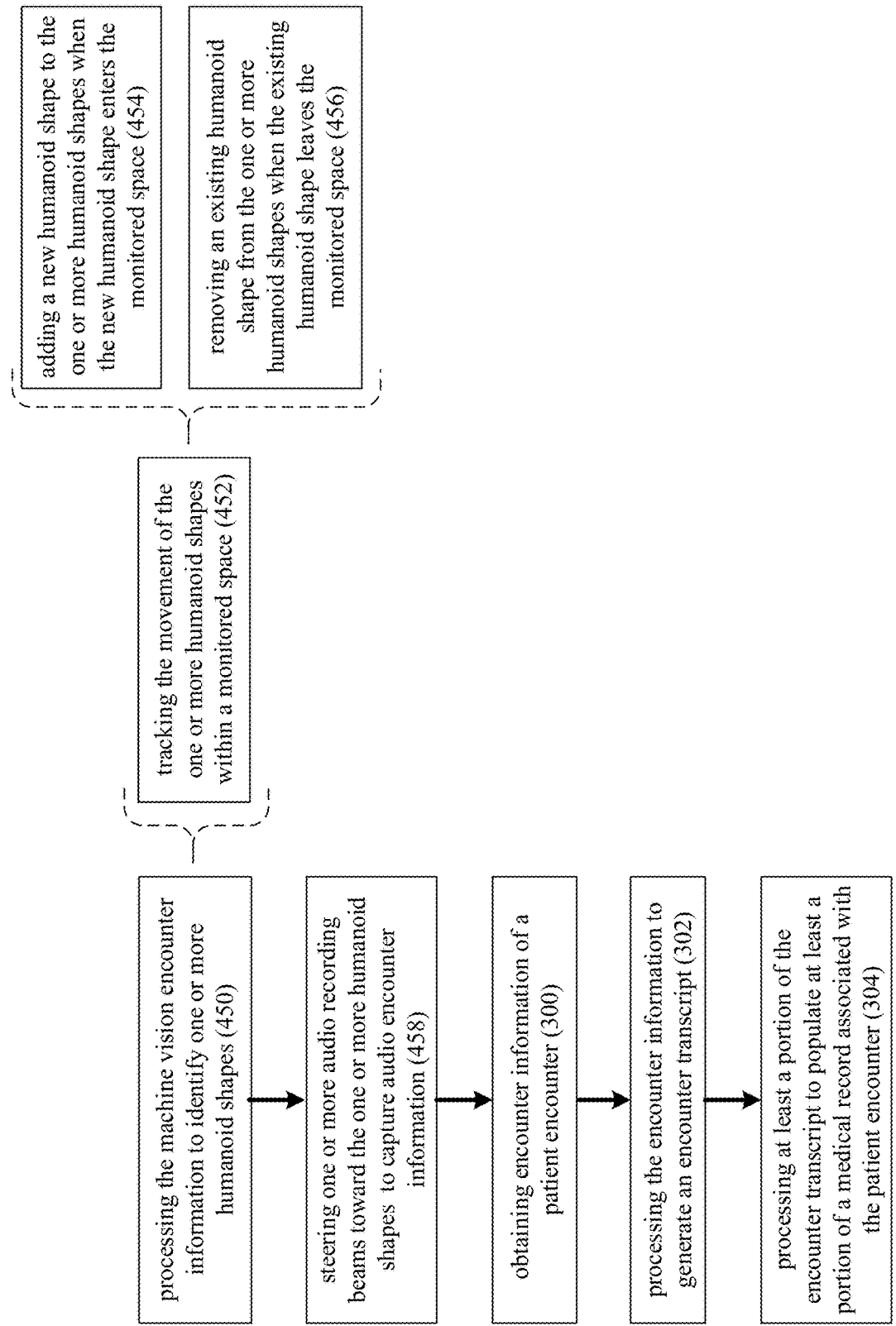
FIG. 7 is a flow chart of another implementation of the ambient cooperative intelligence process of FIG. 1.

Accordingly and referring also to FIG. 7, ambient cooperative intelligence process 10 may process 450 the machine vision encounter information (e.g., machine vision encounter information 102) to identify one or more humanoid shapes. As discussed above, examples of machine vision system 100 generally (and ACI client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system).

When ACI client electronic device 34 includes a visible light imaging system (e.g., an RGB imaging system), ACI client electronic device 34 may be configured to monitor various objects within monitored space 130 by recording motion video in the visible light spectrum of these various objects. When ACI client electronic device 34 includes an invisible light imaging system (e.g., a laser imaging system, an infrared imaging system and/or an ultraviolet imaging system), ACI client electronic device 34 may be configured to monitor various objects within monitored space 130 by recording motion video in the invisible light spectrum of these various objects. When ACI client electronic device 34 includes an X-ray imaging system, ACI client electronic device 34 may be configured to monitor various objects within monitored space 130 by recording energy in the X-ray spectrum of these various objects. When ACI client electronic device 34 includes a SONAR imaging system, ACI client electronic device 34 may be configured to monitor various objects within monitored space 130 by transmitting soundwaves that may be reflected off of these various objects. When ACI client electronic device 34 includes a RADAR imaging system, ACI client electronic device 34 may be configured to monitor various objects within monitored space 130 by transmitting radio waves that may be reflected off of these various objects. When ACI client electronic device 34 includes a thermal imaging system, ACI client electronic device 34 may be configured to monitor various objects within monitored space 130 by tracking the thermal energy of these various objects.

As discussed above, ACI compute system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource.

Accordingly and when processing 450 the machine vision encounter information (e.g., machine vision encounter information 102) to identify one or more humanoid shapes, ambient cooperative intelligence process 10 may be configured to compare the humanoid shapes defined within one or more datasources 118 to potential humanoid shapes within the machine vision encounter information (e.g., machine vision encounter information 102).

When processing 450 the machine vision encounter information (e.g., machine vision encounter information 102) to identify one or more humanoid shapes, ambient cooperative intelligence process 10 may track 452 the movement of the one or more humanoid shapes within the monitored space (e.g., monitored space 130). For example and when tracking 452 the movement of the one or more humanoid shapes within monitored space 130, ambient cooperative intelligence process 10 may add 454 a new humanoid shape to the one or more humanoid shapes when the new humanoid shape enters the monitored space (e.g., monitored space 130) and/or may remove 456 an existing humanoid shape from the one or more humanoid shapes when the existing humanoid shape leaves the monitored space (e.g., monitored space 130).

For example, assume that a lab technician (e.g., encounter participant 242) temporarily enters monitored space 130 to chat with encounter participant 230. Accordingly, ambient cooperative intelligence process 10 may add 454 encounter participant 242 to the one or more humanoid shapes being tracked 452 when the new humanoid shape (i.e., encounter participant 242) enters monitored space 130. Further, assume that the lab technician (e.g., encounter participant 242) leaves monitored space 130 after chatting with encounter participant 230. Therefore, ambient cooperative intelligence process 10 may remove 456 encounter participant 242 from the one or more humanoid shapes being tracked 452 when the humanoid shape (i.e., encounter participant 242) leaves monitored space 130.

Also and when tracking 452 the movement of the one or more humanoid shapes within monitored space 130, ambient cooperative intelligence process 10 may monitor the trajectories of the various humanoid shapes within monitored space 130. Accordingly, assume that when leaving monitored space 130, encounter participant 242 walks in front of (or behind) encounter participant 226. As ambient cooperative intelligence process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by ambient cooperative intelligence process 10.

Ambient cooperative intelligence process 10 may be configured to obtain 300 the encounter information of the patient encounter (e.g., a visit to a doctor's office), which may include machine vision encounter information 102 (in the manner described above) and/or audio encounter information 106.

Ambient cooperative intelligence process 10 may steer 458 one or more audio recording beams (e.g., audio recording beams 220, 222, 224) toward the one or more humanoid shapes (e.g., encounter participants 226, 228, 230) to capture audio encounter information (e.g., audio encounter information 106), wherein audio encounter information 106 may be included within the encounter information (e.g., machine vision encounter information 102 and/or audio encounter information 106).

Specifically and as discussed above, ambient cooperative intelligence process 10 (via modular ACI system 54 and/or audio recording system 104) may utilize one or more of the discrete audio acquisition devices (e.g., audio acquisition devices 202, 204, 206, 208, 210, 212, 214, 216, 218) to form an audio recording beam. For example, modular ACI system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACI system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACI system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230).

Once obtained, ambient cooperative intelligence process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Fully-Autonomous/Semi-Autonomous Scanning:

As discussed above and as shown in FIG. 2, modular ACI system 54 may be configured to automate cooperative intelligence, wherein modular ACI system 54 may include: machine vision system 100 configured to obtain machine vision encounter information 102 concerning a patient encounter; audio recording system 104 configured to obtain audio encounter information 106 concerning the patient encounter; and a compute system (e.g., ACI compute system 12) configured to receive machine vision encounter information 102 and audio encounter information 106 from machine vision system 100 and audio recording system 104 (respectively).

As also discussed above, machine vision system 100 may include but is not limited to: one or more ACI client electronic devices (e.g., ACI client electronic device 34, examples of which may include but are not limited to an RGB imaging system, an infrared imaging system, a ultraviolet imaging system, a laser imaging system, a SONAR imaging system, a RADAR imaging system, and a thermal imaging system).

As also discussed above, audio recording system 104 may include but is not limited to: one or more ACI client electronic devices (e.g., ACI client electronic device 30, examples of which may include but are not limited to a handheld microphone (e.g., one example of a body worn microphone), a lapel microphone (e.g., another example of a body worn microphone), an embedded microphone, such as those embedded within eyeglasses, smart phones, tablet computers and/or watches (e.g., another example of a body worn microphone), and an audio recording device).

Further and as shown in FIG. 3, machine vision system 100 and audio recording system 104 may be combined into one package to form mixed-media ACI device 232. For example, mixed-media ACI device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same.

Modular ACI system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACI device 232 (and machine vision system 100/audio recording system 104 included therein) may be configured to monitor one or more encounter participants (e.g., encounter participants 226, 228, 230) of a patient encounter.

Specifically and as discussed above, machine vision system 100 (either as a stand-alone system or as a component of mixed-media ACI device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

Accordingly, it is foreseeable that one of more of these systems/devices include within modular ACI system 54 (e.g., machine vision system 100, audio recording system 104, mixed-media ACI device 232, and/or audio acquisition devices 202, 204, 206, 208, 210, 212, 214, 216, 218) may need to be calibrated (e.g., initially calibrated and/or subsequently recalibrated).

Figure 8:
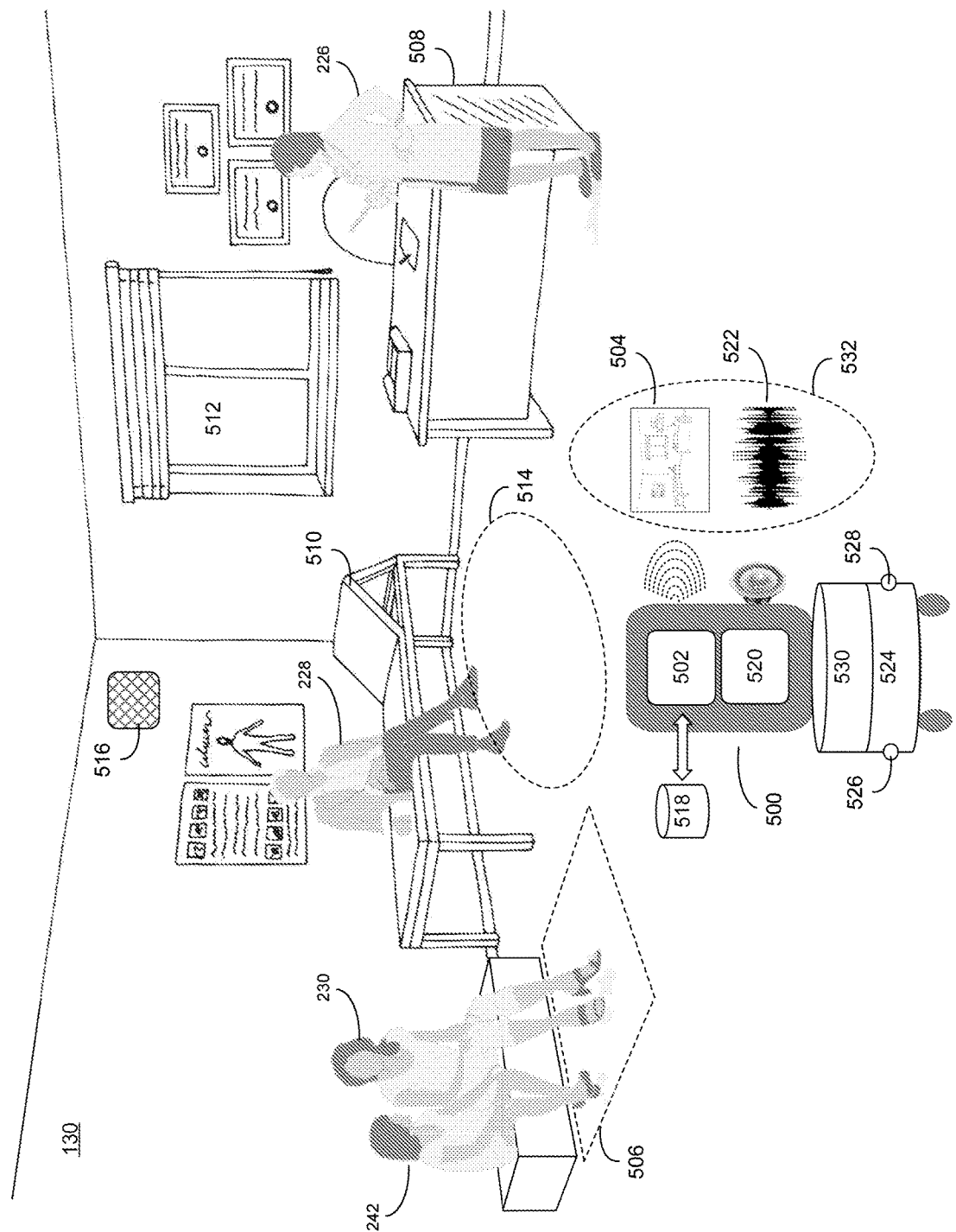
FIG. 8 is a diagrammatic view of an ACI calibration platform.
Figure 9:
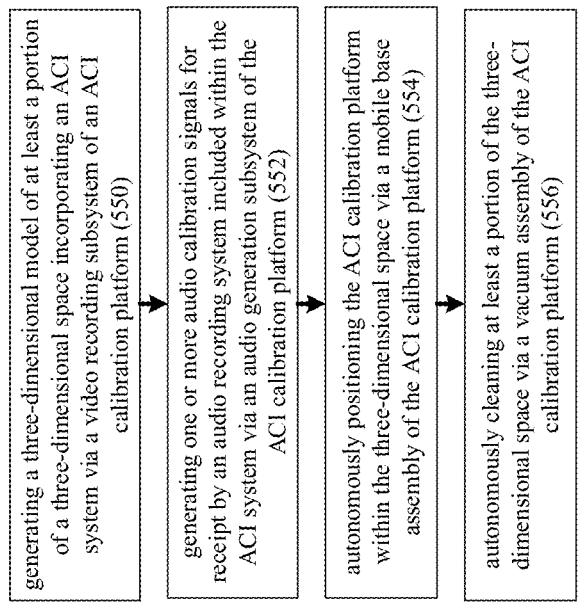
FIG. 9 is a flow chart of one implementation of a process executed by the ACI calibration platform of FIG. 8.
Figure 10:
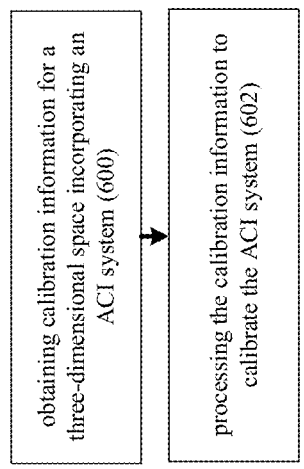
FIG. 10 is a flow chart of another implementation of the ambient cooperative intelligence process of FIG. 1.

Referring also to FIGS. 8-9, such calibration of these one of more systems/devices included within modular ACI system 54 (e.g., machine vision system 100, audio recording system 104, mixed-media ACI device 232, and/or audio acquisition devices 202, 204, 206, 208, 210, 212, 214, 216, 218) may be effectuated via ACI calibration platform 500.

ACI calibration platform 500 may include video recording subsystem 502 configured to generate 550 a three-dimensional model (e.g., three-dimensional model 504) of at least a portion of a three-dimensional space (e.g., monitored space 130) incorporating an ACI system (e.g., modular ACI system 54). ACI calibration platform 500 (generally) and video recording subsystem 502 (specifically) may include (or be interfaced with) machine vision technology, examples of which may include but are not limited to: an RGB imaging system, an infrared imaging system, an ultraviolet imaging system, a laser imaging system, a SONAR imaging system, a RADAR imaging system, and a thermal imaging system.

As discussed above, an example of monitored space 130 may include but is not limited to a clinical environment (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

This three-dimensional model (e.g., three-dimensional model 504) generated by video recording subsystem 502 of ACI calibration platform 500 may be configured to define one or more:

Subspaces: One or more subspaces within the three-dimensional space (e.g., monitored space 130) may be defined within three-dimensional model 504, wherein an example of this subspace may include but is not limited to visitor waiting space 506 (which is shown to include encounter participants 230, 242).

Objects: One or more objects within the three-dimensional space (e.g., monitored space 130) may be defined within three-dimensional model 504, wherein examples of these objects may include but are not limited to: physician desk 508 and examination table 510.

Features: One or more features within the three-dimensional space (e.g., monitored space 130) may be defined within three-dimensional model 504, wherein an example of this feature may include but is not limited to: window 512.

Interaction Zones: One or more interaction zones within the three-dimensional space (e.g., monitored space 130) may be defined within three-dimensional model 504, wherein an example of this interaction zone may include but is not limited to: examination zone 514 (i.e., an area proximate examination table 510).

Noise Sources: One or more noise sources within the three-dimensional space (e.g., monitored space 130) may be defined within three-dimensional model 504, wherein an example of this noise source may include but is not limited to: HVAC supply air vent 516.

ACI calibration platform 500 may be wirelessly coupled to one or more external systems (e.g., modular ACI system 54) and/or one or more external resources (e.g., one or more of datasources 120, 122, 124, 126, 128), thus enabling the transfer of data between ACI calibration platform 500 and these external resources and/or datasources.

Accordingly and through such wireless connectivity, three-dimensional model 504 may be wirelessly transferred from ACI calibration platform 500 to modular ACI system 54 for processing, which will be discussed below in greater detail. Alternatively, three-dimensional model 504 may be transferred from ACI calibration platform 500 to modular ACI system 54 via wired transfer methodologies (e.g., a USB drive; not shown) for processing, which will be discussed below in greater detail.

Video recording system 502 may be configured to interface with an object datasource (e.g., object datasource 518) that may define a plurality of objects that may be located within the three-dimensional space (e.g., monitored space 130). For example, object datasource 518 may define what a desk "looks" like, and what an examination table "looks" like, and what an HVAC vent "looks" like, and what a window "looks" like. This functionality may be accomplished in a fashion similar to the manner in which a facial recognition system knows what a face "looks" like. Depending upon the manner in which ACI calibration platform 500 is configured, object datasource 518 may be a locally-accessible datasource that is resident on ACI calibration platform 500. Alternatively, object datasource 518 may be a remotely-accessible datasource that is resident on modular ACI system 54.

Accordingly and through the use of object datasource 518, ACI calibration platform 500 may produce a three-dimensional model (e.g., three-dimensional model 504) in which the objects included/defined therein may be of a known type (e.g., physician desk 508, examination table 510, window 512, HVAC supply air vent 516), which may be accomplished via tagging/metadata.

ACI calibration platform 500 may include audio generation subsystem 520 configured to generate 552 one or more audio calibration signals (e.g., audio calibration signal 522) for receipt by an audio recording system (e.g., audio recording system 104) included within the ACI system (e.g., modular ACI system 54). ACI calibration platform 500 (generally) and audio generation subsystem 520 (specifically) may include (or be interfaced with) audio rendering technology, an example of which may include but is not limited to a speaker assembly.

The one or more audio calibration signals (e.g., audio calibration signal 522) may include one or more of:

Noise Signal: An example of audio calibration signal 522 may include but is not limited to: a white noise signal. As is known in the art, a white noise signal is a random signal having equal intensity at all frequencies, giving it a constant power spectral density. The term is used, with this or similar meanings, in many scientific and technical disciplines, including physics, acoustical engineering, telecommunications, and statistical forecasting. White noise refers to a statistical model for signals and signal sources, rather than to any specific signal.

Sinusoid Signal: An example of audio calibration signal 522 may include but is not limited to: a sinusoid. A sinusoid signal is a signal fully characterized by a mathematical function that describes a smooth periodic oscillation having a fixed frequency. It is named after the function sine. Sinusoids often occur in pure and applied mathematics, as well as physics, engineering, and signal processing.

Multi-Frequency Signal: An example of audio calibration signal 522 may include but is not limited to: a sweeping sinusoid. A sweeping sinusoid signal is a signal fully characterized by a mathematical function that describes a smooth periodic oscillation having a frequency that varies with time (typically between two frequencies, such as a logarithmic sweep from 20 Hz to 20 kHz in acoustic applications).

Impulse Function: An example of audio calibration signal 522 may include but is not limited to: an impulse function. An impulse function is a function that is zero everywhere but at the origin, where the amplitude is infinitely high.

ACI calibration platform 500 may include mobile base assembly 524 configured to autonomously position 554 ACI calibration platform 500 within the three-dimensional space (e.g., monitored space 130). Accordingly, ACI calibration platform 500 may be configured to move in an automated and controlled fashion within monitored space 130 (e.g., in a fashion similar to that of a robotic autonomous vacuum). For example, ACI calibration platform 500 may include the above-described machine vision technology to enable ACI calibration platform 500 to navigate through monitored space 130 via the use of mobile base assembly 524. Additionally, ACI calibration platform 500 (generally) and mobile base assembly 524 (specifically) may include one of more impact sensors (e.g., impact sensors 526, 528) that sense impact with various objects within the monitored space 130 (e.g., walls, doors, furniture) so that, upon sensing such an impact, the direction in which ACI calibration platform 500 in travelling may be adjusted (e.g., reversed).

ACI calibration platform 500 may include cleaning assembly 530 configured to autonomously clean 556 at least a portion of the three-dimensional space (e.g., monitored space 130). Examples of cleaning assembly 530 may include:

Vacuum Assembly: For example, cleaning assembly 530 may be configured to vacuum the floor of monitored space 130.

Mop Assembly: For example, cleaning assembly 530 may be configured to mop the floor of monitored space 130.

Sterilizing Assembly: For example, cleaning assembly 530 may be configured to sterilize the floor of monitored space 130 via e.g., steam generation or ultraviolet light.

While ACI calibration platform 500 is described above as being capable of autonomously moving within monitored space 130 (via mobile base assembly 524), this is for illustrative purpose only and is not intended to be a limitation of this disclosure, as other configurations are possible and are considered to be within the scope of this disclosure. For example, ACI calibration platform 500 may be configured to be manually positioned within the three-dimensional space (e.g., monitored space 130). Therefore, ACI calibration platform 500 may be included within (or a portion of) a handheld client electronic device (such as a smart telephone or a tablet computer).

As is known in the art, such client electronic devices typically include machine vision technology (such as visible light cameras) and audio rendering technology (such as one or more speaker assemblies) that enable the generation 550, 552 of three-dimensional model 504 and/or audio calibration signal 522 In such an implementation, ACI calibration platform 500 may be manually manipulated (i.e., moved/positioned) within monitored space 130 by a user, wherein the user may move ACI calibration platform 500 within monitored space 130 to generate 550 three-dimensional model 504 and/or generate 552 audio calibration signal 522 from all of the appropriate/required positions within monitored space 130.

ACI System Calibration:

As discussed above, ACI calibration platform 500 may be wirelessly coupled to one or more external systems (e.g., modular ACI system 54) and/or one or more external resources (e.g., one or more of datasources 120, 122, 124, 126, 128), thus enabling the transfer of data between ACI calibration platform 500 and these external resources and/or datasources. Accordingly and through such wireless connectivity, three-dimensional model 504 may be wirelessly transferred from ACI calibration platform 500 to modular ACI system 54 for processing. Alternatively, three-dimensional model 504 may be transferred from ACI calibration platform 500 to modular ACI system 54 for processing via non-wireless transfer methodologies, such as via a portable data transfer device (e.g., a USB drive; not shown).

Accordingly, ambient cooperative intelligence process 10 may obtain 600 calibration information (e.g., calibration information 532) for a three-dimensional space (e.g., monitored space 130) incorporating an ACI system (e.g., modular ACI system 54). As discussed above, this calibration information may be obtained from an ACI calibration platform (e.g., ACI calibration platform 500). This calibration information (e.g., calibration information 532) may include three-dimensional model 504 and one or more audio calibration signals (e.g., audio calibration signal 522).

As discussed above, ACI calibration platform 500 may generate three-dimensional model 504 for at least a portion of monitored space 130 incorporating an ACI system (e.g., modular ACI system 54), wherein three-dimensional model 504 may be configured to define one or more:

Subspaces: One or more subspaces within the three-dimensional space (e.g., monitored space 130) may be defined within three-dimensional model 504, wherein an example of this subspace may include but is not limited to visitor waiting space 506 (which is shown to include encounter participants 230, 242).

Objects: One or more objects within the three-dimensional space (e.g., monitored space 130) may be defined within three-dimensional model 504, wherein examples of these objects may include but are not limited to: physician desk 508 and examination table 510.

Features: One or more features within the three-dimensional space (e.g., monitored space 130) may be defined within three-dimensional model 504, wherein an example of this feature may include but is not limited to: window 512.

Interaction Zones: One or more interaction zones within the three-dimensional space (e.g., monitored space 130) may be defined within three-dimensional model 504, wherein an example of this interaction zone may include but is not limited to: examination zone 514 (i.e., an area proximate examination table 510).

Noise Sources: One or more noise sources within the three-dimensional space (e.g., monitored space 130) may be defined within three-dimensional model 504, wherein an example of this noise source may include but is not limited to: HVAC supply air vent 516.

As discussed above, these one or more audio calibration signals (e.g., audio calibration signal 522) may include one or more of:

Noise Signal: An example of audio calibration signal 522 may include but is not limited to: a white noise signal. As is known in the art, a white noise signal is a random signal having equal intensity at all frequencies, giving it a constant power spectral density. The term is used, with this or similar meanings, in many scientific and technical disciplines, including physics, acoustical engineering, telecommunications, and statistical forecasting. White noise refers to a statistical model for signals and signal sources, rather than to any specific signal.

Sinusoid Signal: An example of audio calibration signal 522 may include but is not limited to: a sinusoid. A sinusoid signal is a signal fully characterized by a mathematical function that describes a smooth periodic oscillation having a fixed frequency. It is named after the function sine. Sinusoids often occur in pure and applied mathematics, as well as physics, engineering, and signal processing.

Multi-Frequency Signal: An example of audio calibration signal 522 may include but is not limited to: a sweeping sinusoid. A sweeping sinusoid signal is a signal fully characterized by a mathematical function that describes a smooth periodic oscillation having a frequency that varies with time (typically between two frequencies, such as a logarithmic sweep from 20 Hz to 20 kHz in acoustic applications).

Impulse Function: An example of audio calibration signal 522 may include but is not limited to: an impulse function. An impulse function is a function that is zero everywhere but at the origin, where the amplitude is infinitely high.

Specifically, three-dimensional model 504 may be wirelessly transferred (or transferred via wired transfer) from ACI calibration platform 500 to modular ACI system 54 in e.g., the manners described above. Additionally, the one or more audio calibration signals (e.g., audio calibration signal 522) may be acoustically transferred from ACI calibration platform 500 to modular ACI system 54. For example, audio calibration signal 522 may be rendered via e.g., a speaker assembly included within ACI calibration platform 500, wherein audio calibration signal 522 may be acoustically transferred through the air of monitored space 130 and "heard" by modular ACI system 54 via e.g., audio acquisition devices 202, 204, 206, 208, 210, 212, 214, 216, 218).

Once the calibration information (e.g., calibration information 532) is obtained 600, ambient cooperative intelligence process 10 may process 602 this calibration information (e.g., calibration information 532) to calibrate (e.g., either initially or subsequently) the ACI system (e.g., modular ACI system 54).

Specifically, the one or more audio calibration signals (e.g., audio calibration signal 522) may be utilized, in whole or in part, to calibrate one or more audio acquisition devices (e.g., audio acquisition devices 202, 204, 206, 208, 210, 212, 214, 216, 218) within the three-dimensional space (e.g., monitored space 130).

As is known in the art, the performance of audio acquisition devices (e.g., audio acquisition devices 202, 204, 206, 208, 210, 212, 214, 216, 218) may vary over time. Naturally, such audio acquisition devices may totally fail and simply not work anymore (which is comparatively simple to detect). However, such audio acquisition devices may not completely fail and may only suffer from performance drift where the ability of an older audio acquisition device to detect e.g., higher frequency signals is diminished (in a fashion similar to the manner in which the hearing of a human declines as they get older). Accordingly and through the use of the one or more audio calibration signals (e.g., audio calibration signal 522), the performance of audio acquisition devices (e.g., audio acquisition devices 202, 204, 206, 208, 210, 212, 214, 216, 218) may be determined/measured and compensated (if need be).

As discussed above, modular ACI system 54 may be configured to steer one or more audio recording beams (e.g., audio recording beams 220, 222, 224) toward one or more encounter participants (e.g., encounter participants 226, 228, 230) of the above-described patient encounter, wherein modular ACI system 54 may be configured to utilize one or more of the discrete audio acquisition devices (e.g., audio acquisition devices 202, 204, 206, 208, 210, 212, 214, 216, 218) to form these audio recording beams (e.g., audio recording beams 220, 222, 224).

As discussed above, an example of audio calibration signal 522 may be a white noise signal (e.g., a random signal having equal intensity at all frequencies). Accordingly and as ACI calibration platform 500 is moved (and continuously repositioned) within monitored space 130, audio generation subsystem 520 within ACI calibration platform 500 may render audio calibration signal 522 that is (in this example) a white noise signal having equal spectral intensity from 20

Hz to 20 kHz. Further assume that audio acquisition devices 202, 204, 206, 208, 210, 212, 214, 216, 218 are designed to have a flat frequency response (i.e., be equally sensitive) to signals in the range of 100 Hz to 5 kHz. Accordingly and in order to test the performance of audio acquisition devices 202, 204, 206, 208, 210, 212, 214, 216, 218, ACI calibration platform 500 may move (or be moved) to a sufficient number of locations within monitored space 130 to ensure spatial coverage of the acoustic environment (e.g., by measuring a number of acoustic paths from typical interaction zones to the various ACI devices (e.g., audio acquisition devices 202, 204, 206, 208, 210, 212, 214, 216, 218) within monitored space 130).

Since (in this example) audio calibration signal 522 is a white noise signal having equal spectral intensity from 20 Hz to 20 kHz, the frequency response of each of audio acquisition devices 202, 204, 206, 208, 210, 212, 214, 216, 218 from 100 Hz to 5 kHz should be flat (i.e., have equal intensity). In the event that one of audio acquisition devices 202, 204, 206, 208, 210, 212, 214, 216, 218 is not producing any signal, this particular audio acquisition device may have failed and may likely need replacement.

And in the event that one of audio acquisition devices 202, 204, 206, 208, 210, 212, 214, 216, 218 is performing oddly, this particular audio acquisition device may need to be compensated. For example:

- if audio acquisition device 202 is over-sensitive at 1 kz and is producing an output signal that is 6 db above where it is expected to be @ 1 kHz, ambient cooperative intelligence process 10 may attenuate the output signal provided by audio acquisition device 202 by a factor of 6 db @ 1 kHz.
- if audio acquisition device 206 is under-sensitive at 3 kz and is producing an output signal that is 8 db below where it is expected to be @ 3 kHz, ambient cooperative intelligence process 10 may be configured to amplify the output signal provided by audio acquisition device 206 by a factor of 8 db @ 3 kHz.

Further, the three-dimensional model (e.g., three-dimensional model 504) may be utilized, in whole or in part, to steer one or more audio recording beams (e.g., audio recording beams 220, 222, 224) within the three-dimensional space (e.g., monitored space 130).

As discussed above and through the use of object datasource 518, ACI calibration platform 500 may produce a three-dimensional model (e.g., three-dimensional model 504) in which the objects included/defined therein may be of a known type (e.g., physician desk 508, examination table 510, window 512, HVAC supply air vent 516), which may be accomplished via tagging/metadata. Accordingly, ambient cooperative intelligence process 10 may determine acoustic propagation channel information for the purpose of e.g., robust automated speech recognition, signal enhancement, audio recording beam forming, acoustic echo cancellation, null steering and blind source separation. This acoustic path information may be associated with the spatial information defined within three-dimensional model 504.

As is known in the art, echo cancellation is a method for improving signal quality by removing echo after it is already present. This method may be called acoustic echo suppression (AES) and acoustic echo cancellation (AEC), and more rarely and in context of telecommunications line echo cancellation (LEC). In some cases, these terms are more precise, as there are various types and causes of echo with unique characteristics, including acoustic echo (sounds from a loudspeaker being reflected, coupled to and recorded by a microphone, which can vary substantially over time) and line echo (electrical echo signals caused by e.g., coupling between the sending and receiving wires, impedance mismatches, electrical reflections, etc., which varies much less than acoustic echo). Accordingly and in this configuration, such echo cancellation methodologies may be utilized to e.g., eliminate the couple signal of a second speaker that appears in the audio recording beam steered at a closely-positioned first speaker; while also eliminating the coupled signal of the first speaker that appears in the audio recording beam steered at the closely-positioned second speaker.

As is known in the art, null-steering precoding is a method of spatial signal processing by which a multiple antenna transmitter may null multiuser interference signals in wireless communications, wherein null-steering precoding may mitigate the impact of background noise and unknown user interference. In particular, null-steering precoding may be a method of beamforming for narrowband signals that may compensate for delays of receiving signals from a specific source at different elements of an antenna array. In general and to improve performance of the antenna array, incoming signals may be summed and averaged, wherein certain signals may be weighted and compensation may be made for signal delays.

As is known in the art, blind source separation is the separation of a set of source signals from a set of mixed signals, without the aid of information (or with very little information) about the source signals or the mixing process. Since the chief difficulty of blind source separation is its underdetermination, methods for blind source separation generally seek to narrow the set of possible solutions in a way that is unlikely to exclude the desired solution. In one approach, exemplified by principal and independent component analysis, one seeks source signals that are minimally correlated or maximally independent in a probabilistic or information-theoretic sense. A second approach, exemplified by nonnegative matrix factorization, is to impose structural constraints on the source signals.

As discussed above, three-dimensional model 504 may be configured to define one or more:

- Subspaces: One or more subspaces within the three-dimensional space (e.g., monitored space 130) may be defined within three-dimensional model 504, wherein an example of this subspace may include but is not limited to visitor waiting space 506 (which is shown to include encounter participants 230, 242).
- Objects: One or more objects within the three-dimensional space (e.g., monitored space 130) may be defined within three-dimensional model 504, wherein examples of these objects may include but are not limited to: physician desk 508 and examination table 510.
- Features: One or more features within the three-dimensional space (e.g., monitored space 130) may be defined within three-dimensional model 504, wherein an example of this feature may include but is not limited to: window 512.
- Interaction Zones: One or more interaction zones within the three-dimensional space (e.g., monitored space 130) may be defined within three-dimensional model 504, wherein an example of this interaction zone may include but is not limited to: examination zone 514 (i.e., an area proximate examination table 510).
- Noise Sources: One or more noise sources within the three-dimensional space (e.g., monitored space 130) may be defined within three-dimensional model 504, wherein an example of this noise source may include but is not limited to: HVAC supply air vent 516.

Each of the specific subspaces, objects, features, interaction zones and noise sources defined within three-dimensional model 504 may have positive/negative impact concerning the manner in which audio recording beams (e.g., audio recording beams 220, 222, 224) may be steered within the three-dimensional space (e.g., monitored space 130).

For example and with respect to visitor waiting space 506 (which is shown to include encounter participants 230, 242), ambient cooperative intelligence process 10 may disfavor steering audio recording beams (e.g., audio recording beams 220, 222, 224) toward visitor waiting space 506, as this is a waiting area and it is less likely that substantive information may be extracted from conversations that are occurring in this area.

Conversely and with respect to physician desk 508 and examination table 510, ambient cooperative intelligence process 10 may favor steering audio recording beams (e.g., audio recording beams 220, 222, 224) toward physician desk 508 and examination table 510, as it is more likely that substantive information may be extracted from conversations that are occurring in these areas.

With respect to window 512, ambient cooperative intelligence process 10 may disfavor steering audio recording beams (e.g., audio recording beams 220, 222, 224) toward window 512, as this is a hard surface and it is more likely that high levels of reflection/echo/noise may be included within information captured with an audio recording beam directed toward window 512.

Conversely and with respect to examination zone 514 (i.e., an area proximate examination table 510), ambient cooperative intelligence process 10 may favor steering audio recording beams (e.g., audio recording beams 220, 222, 224) toward examination zone 514, as it is more likely that substantive information may be extracted from conversations that are occurring in this area.

From the above-described calibration step, a model that locates objects within the three-dimensional space (e.g., monitored space 130) may be defined, wherein this model may aid the natural language understanding functionality of ambient cooperative intelligence process 10. For example, if ambient cooperative intelligence process 10 identifies sound coming from a location that corresponds to an examination bed, this information may be very useful for the natural language understanding functionality of ambient cooperative intelligence process 10, particularly if modular ACI system 54 does not include machine vision.

With respect to HVAC supply air vent 516, ambient cooperative intelligence process 10 may disfavor steering audio recording beams (e.g., audio recording beams 220, 222, 224) toward HVAC supply air vent 516, as this is a noisy object and it is more likely that high levels of noise may be included within information captured with an audio recording beam directed toward HVAC supply air vent 516.

Non-Medical Applications:

As discussed above, while ambient cooperative intelligence process 10 was described above as being utilized to automate the collection and processing of clinical encounter information to generate/store/distribute medical records, this is for illustrative purposes only and is not intended to be a limitation of this disclosure, as other configurations are possible and are considered to be within the scope of this disclosure. Accordingly, such encounter information may include but are not limited to the following examples.

Financial Information:

For example, ambient cooperative intelligence process 10 generally (and/or ACD system 54 specifically) may be configured to automate the collection and processing of financial data that is generated during an encounter in which financial information is discussed. An example of such an encounter may include but is not limited to a meeting between an individual and a financial advisor. For example, ambient cooperative intelligence process 10 may be configured to supplement/complement a financial advisor's knowledge by recommending products, answering questions and making offers based on the conversation that the financial advisor is having with a client in essentially real time, as well as completing various forms, mortgage applications, stock purchase/sale orders, estate planning documents, etc.

Benefits: The benefits achievable by ambient cooperative intelligence process 10 when configured to process financial information may be considerable. For example and as is understandable, financial advisors may not know all things concerning e.g., financial and investment instruments. Accordingly, ambient cooperative intelligence process 10 (when configured to process financial information) may monitor a conversation between the financial advisor and the client. Ambient cooperative intelligence process 10 may then utilize natural language processing and artificial intelligence to identify issues/questions within the conversation and leverage collective knowledge to provide pertinent information to the financial advisor.

For example, assume that a client visits a financial advisor seeking financial advice concerning tax free/tax deferred retirement savings. Accordingly and through the use of the various systems described above (e.g., audio input device 30, display device 32, machine vision input device 34, and audio rendering device 116), ambient cooperative intelligence process 10 (when configured to process financial information) may monitor the conversation between the financial advisor and the client. Assuming that this is the first time that this client is meeting with his financial advisor, the information obtained during this initial meeting may be parsed and used to populate the various fields of a client intake form. For example, the client may identify themself and their name may be entered into the client intake form. Additionally, ambient cooperative intelligence process 10 may be configured to define a voiceprint and/or face print for the client so that e.g. in the future this voiceprint and/or face print may be utilized to authenticate the client's identity when they want to access their data. Additionally, when the client identifies e.g. their age, their marital status, their spouse's name, their spouse's age, and whether or not they have children and (if so) the age of their children, all of this information may be used to populate this client intake form.

Continuing with the above stated example, assume that the client asks about tax-free/tax-deferred retirement savings plans. The financial advisor may then ask them what their income was last year. As ambient cooperative intelligence process 10 may be monitoring this conversation via audio input device 30, ambient cooperative intelligence process 10 may "hear" that the client is interested in tax-free/tax-deferred retirement savings plans and what their income level is. Accordingly and through the use of the above-described natural language processing and artificial intelligence, ambient cooperative intelligence process 10 may determine whether or not the client qualifies for a 401(k) retirement plan, a pre-tax/post-tax traditional IRA plan, and/or a pre-tax/post-tax Roth IRA plan. Upon making such a determination, ambient cooperative intelligence process 10 may provide supplemental information to the financial advisor so that the financial advisor may provide guidance to the client.

For example, ambient cooperative intelligence process 10 may render (on display device 32) a list of the tax-free/tax-deferred retirement savings plans for which the client qualifies. Additionally/alternatively, this information may be audibly rendered (e.g. covertly into an earbud worn by the financial advisor) so that the financial advisor may provide such information to the client.

Accordingly and through the use of such a system, ambient cooperative intelligence process 10 (when configured to process financial information) may monitor the conversation between (in this example) the financial advisor and a client to e.g. gather information and populate client intake forms, generate voice prints and/or face prints for client authentication, listen to inquiries made by the client, and provide responses to those inquiries so that the financial advisor may provide guidance to the client.

Additionally, ambient cooperative intelligence process 10 may be configured to monitor the advice that the financial advisor is providing to the client and confirm the accuracy of the same, wherein covert corrections/notifications may be provided to the financial advisor in the event that the financial advisor misspoke (e.g., advising the client that they qualify for a retirement plan when they actually do not qualify).

Further, ambient cooperative intelligence process 10 may be configured to provide guidance to the financial advisor/client even when such guidance is not sought. For example, if this client said that they have children, ambient cooperative intelligence process 10 may prompt the financial advisor to inquire as to what college savings plans (e.g. 529s) they have in place for their children. And if none are in place, the financial advisor may be prompted to explain the tax benefits of such plans.

Further still, ambient cooperative intelligence process 10 may be configured to covertly provide information to the financial advisor that may assist in building a relationship between the financial advisor and client. For example, assume that the client explained that his wife's name was Jill (during the first meeting between the client and the financial advisor) and the client explained that he and his wife were going to be visiting Italy over the summer. Assume that the client returns to meet with the financial advisor in the fall. During the first visit, ambient cooperative intelligence process 10 may (as discussed above) populate a client intake form that identifies the client spouse as Jill. Further, ambient cooperative intelligence process 10 may make a note that the client and Jill are going to be visiting Italy in the summer of 2020. Assuming that this follow-up meeting is after the summer of 2020, ambient cooperative intelligence process 10 may covertly prompt the financial advisor to ask the client if he and Jill enjoyed Italy, thus enabling the establishment of goodwill between the client and the financial advisor.

Ambient cooperative intelligence process 10 may further be configured to auto-populate forms that may be required based upon the needs of the client. For example, if the client needs to fill out a certain tax form concerning an IRA rollover, ambient cooperative intelligence process 10 may be configured to obtain necessary information based on a conversation between the financial advisor and the client and/or proactively obtain the required information from a datasource accessible by ambient cooperative intelligence process 10, populate the appropriate form needed to effectuate e.g., the IRA rollover with the data obtained from the datasource, and render (e.g. print) the populated form so that the client may execute the same.

Ambient cooperative intelligence process 10 may further be configured to effectuate the functionality of a digital assistant, wherein ambient cooperative intelligence process 10 may monitor the conversation between (in this example) the financial advisor and the client so that items that were mentioned may be flagged for follow-up. For example, assume that during the above-described conversation between the financial advisor and the client that the client stated that they are interested in setting up 529 college savings accounts for their children and they asked the financial advisor to provide them information concerning the same. Accordingly, ambient cooperative intelligence process 10 may enter (e.g. into a client-specific to do list) "Send 529 information to the Smith family". Additionally, in the event that the client says they would like to have a follow-up meeting in three weeks to chat about 529's, ambient cooperative intelligence process 10 may schedule a meeting within the calendar of the financial advisor for such a discussion.

Legal Information:

For example, ambient cooperative intelligence process 10 generally (and/or ACD system 54 specifically) may be configured to automate the collection and processing of legal data that is generated during an encounter in which legal information is discussed. An example of such an encounter may include but is not limited to a meeting between a legal professional and a person whom they are representing. For example, ambient cooperative intelligence process 10 may be configured to supplement/complement a legal professional's knowledge by recommending strategies, answering questions and providing advice based on the conversation that the legal professional is having with their client in essentially real time, as well as completing hearing/deposition transcripts, warrants, court orders/judgements, various applications for the foregoing and other items, etc.

Benefits: The benefits achievable by ambient cooperative intelligence process 10 when configured to process legal information may be considerable. For example and as is understandable, legal professionals may not know all things concerning e.g., various legal situations, events and procedures. Accordingly, ambient cooperative intelligence process 10 (when configured to process legal information) may monitor a conversation between the legal professional and the client. Ambient cooperative intelligence process 10 may then utilize natural language processing and artificial intelligence to identify issues/questions within the conversation and leverage collective knowledge to provide pertinent information to the legal professional.

For example, assume that a deposition is occurring where a defendant in a lawsuit (who is being represented by a first group of attorneys) is being asked questions by the plaintiff in the law suit (who is being represented by a second group of attorneys). Accordingly and through the use of the various systems described above (e.g., audio input device 30, display device 32, machine vision input device 34, and audio rendering device 116), ambient cooperative intelligence process 10 (when configured to process legal information) may monitor the conversation between the defendant/first group of attorneys and the plaintiff/second group of attorneys. In such a situation, ambient cooperative intelligence process 10 (when configured to process legal information) may be configured to effectuate the functionality of a court transcriptionist.

For example, the participants in the deposition may be asked to identify themselves (e.g. provide name and title). Ambient cooperative intelligence process 10 may use this information to populate an attendance log concerning the deposition and may be configured to define a voiceprint and/or face print for each attendee of the deposition.

Accordingly and once the deposition actually starts, ambient cooperative intelligence process 10 may monitor the deposition and may (via the above described voice prints/face prints) diarize the same, essentially replicating the functionality of a court transcriptionist. Basically, ambient cooperative intelligence process 10 may generate a diary of the deposition proceeding that reads like a movie script, wherein e.g. each spoken statement is transcribed and the speaker of that spoken statement is identified (via the voiceprint/face print).

Additionally and through the use of the above-describe natural language processing and artificial intelligence, traditional legal tasks may be efficiently effectuated. For example, suppose that (during the deposition) an objection is made and a piece of case law is cited as the basis for the objection. If the non-objecting attorney believes that this piece of case law is no longer valid (e.g. due to it being overturned by a higher court), the non-objecting attorney may ask ambient cooperative intelligence process 10 (when configured to process legal information) to determine the status of the relied-upon piece of case law (i.e., whether the piece of case law is still valid or has been overturned). Ambient cooperative intelligence process may then provide an answer to the non-objecting attorney (e.g., the case is still valid or the case was overturned by the $1^{st}$ Circuit Court of Appeals in 2016, which was affirmed by the US Supreme Court in 2017).

Telecom Information:

For example, ambient cooperative intelligence process 10 generally (and/or ACD system 54 specifically) may be configured to automate the collection and processing of telecom data that is generated during an encounter between a caller and a sales/service representative. An example of such an encounter may include but is not limited to a telephone call and/or chat session between a sales/service representative and a customer who is having a problem with their cable television service. For example, ambient cooperative intelligence process 10 may be configured to supplement/complement a service representative's knowledge by recommending plans/products, trouble-shooting procedures, answering questions and providing advice based on the conversation that the service representative is having with their customer in essentially real time.

Benefits: The benefits achievable by ambient cooperative intelligence process 10 when configured to process telecom information may be considerable. For example and as is understandable, sales/service representatives may not know all things concerning e.g., various service plans, available products, trouble-shooting procedures, and warranty coverage. Accordingly, ambient cooperative intelligence process 10 (when configured to process telecom information) may monitor a conversation (e.g., voice or text) between the service representative and the caller. Ambient cooperative intelligence process 10 may then utilize natural language processing and artificial intelligence to identify issues/questions within the conversation and leverage collective knowledge to provide pertinent information to the telecom salesperson.

For example, assume that a user of a cable television service is having a difficult time tuning to one of their pay channels within their cable TV channel list. Accordingly, this user may call up (or message) their cable television service and chat with a customer service representative. Ambient cooperative intelligence process 10 (when configured to process telecom information) may e.g. utilize caller ID, IP addresses and/or voice prints to identify the caller and obtain information concerning their account, their location, their equipment, their service plan, etc.

Assume for this example that the caller explains to the service representative that they cannot tune their cable box to the desired channel. Ambient cooperative intelligence process 10 may e.g. first confirm that their current service plan includes the channel that the caller is trying to access. In the event that the service plan does not include such channel, ambient cooperative intelligence process 10 may notify the service representative (e.g. via a text-based message visible on a display accessible by the service representative or via an earbud) that the channel is not included in their service plan. Ambient cooperative intelligence process 10 may then provide information to the service representative concerning which service plans include the channel about which the caller is inquiring to see if e.g., they want to upgrade/change their plan to one that includes the channel in question.

In the event that the channel is indeed included in the current service plan of the caller, ambient cooperative intelligence process 10 may begin to provide prompts to the service representative concerning a troubleshooting procedure that may be utilized to identify the problem. For example, ambient cooperative intelligence process 10 (via e.g. a display or an earbud) may provide the service representative with a sequence of steps that the caller can perform in order to (hopefully) rectify the situation. For example, the service representative may instruct the caller to first unplug the cable box from the electrical outlet and let it sit for 30 seconds and then plug it in so that it may reboot. In the event that this procedure does not fix the problem, the list provided by ambient cooperative intelligence process 10 may instruct the service representative to send a reset signal to the cable box in question. In the event that this procedure does not fix the problem, ambient cooperative intelligence process 10 may determine that a new cable box is needed and may assist the service representative in scheduling a service call so that the faulty cable box may be replaced by a service technician.

Retail Information:

For example, ambient cooperative intelligence process 10 generally (and/or ACD system 54 specifically) may be configured to automate the collection and processing of retail data that is generated during an encounter in which retail information is discussed. An example of such an encounter may include but is not limited to a meeting between a salesclerk at a department store and a person interested in purchasing a particular product. For example, ambient cooperative intelligence process 10 may be configured to supplement/complement a salesclerk's knowledge by recommending products, answering questions and providing advice based upon the conversation that the salesclerk is having with their customer in essentially real time, as well as enabling checkout, completing work order forms, financial/sales agreements, product order forms, warranty forms, etc.

Benefits: The benefits achievable by ambient cooperative intelligence process 10 when configured to process retail information may be considerable. For example and as is understandable, salesclerks may not know all things concerning e.g., the assortment of products offered and the location of the same. Accordingly, ambient cooperative intelligence process 10 (when configured to process retail information) may monitor a conversation between the salesclerk and the customer. Ambient cooperative intelligence process 10 may then utilize natural language processing and artificial intelligence to identify issues/questions within the conversation and leverage collective knowledge to provide pertinent information to the salesclerk.

For example, assume that a customer goes to a local department store and they are looking for several items, including an electric drill. So this customer approaches a salesclerk and asks them if they sell electric drills and, if so, where they are. Ambient cooperative intelligence process 10 (when configured to process retail information) may monitor this conversation and identify the issues that need to be addressed through the use of the above-described natural language processing and artificial intelligence. For example, ambient cooperative intelligence process 10 may identify the phrase "electric drill" within the statement made by the customer and may examine inventory records for the department store and determine that the department store does indeed sell electric drills. Further, ambient cooperative intelligence process 10 may determine that the customer is asking about the location of these electric drills and, upon checking product stocking charts for the department store, may determine that electric drills are in the hardware section (aisle 23, bays 16-20).

Additionally, ambient cooperative intelligence process 10 may be configured to address additional questions that the customer may have, such as 'What electric drills the have that cost under $30?", "What electric drill has the longest warranty?", "What electric drills do you have from DeWalt?" and "Do you have drill bits for drilling into cement?". When providing answers concerning these questions raised by the customer, ambient cooperative intelligence process 10 may overtly provide the information onto a display screen (e.g. a handheld electronic device) so that the customer may review the same. Alternatively, ambient cooperative intelligence process 10 may covertly provide the information in an earbud so that the salesclerk may verbally provide the information to the customer.

Further, assume that a family goes into a local wireless carrier store to inquire about cell phones and cell phone plans. Accordingly and through the use of the various systems described above (e.g., audio input device 30, display device 32, machine vision input device 34, and audio rendering device 116), ambient cooperative intelligence process 10 (when configured to process retail information) may monitor the conversation between the family and salesclerk and provide guidance and insight with respect to such conversation through the use of the above-described natural language processing and artificial intelligence. For example, assume that the family asks the salesclerk if there are any sales/promotions on the latest iPhones. If so, ambient cooperative intelligence process 10 (when configured to process retail information) may covertly provide a list of sales/promotions to the salesclerk via e.g., an earbud assembly or may overly provide a list of sales/promotions to the salesclerk via e.g., a client electronic device (e.g., a smart phone, a tablet, a laptop, or a display).

Additionally, assume that the family inquires as to what is the best phone to buy and/or what is the best data plan to be on when you do extensive international traveling. Accordingly, ambient cooperative intelligence process 10 (when configured to process retail information) may e.g. render a list of applicable phones/data plans on a client electronic device (e.g. a smart phone, a tablet, a laptop, or display) so that such options may be reviewed with the salesclerk. Further, in the event that ambient cooperative intelligence process 10 determines that one or more members of the family is interested in a cellular telephone that is not compatible with the cellular networks in various countries around the world, ambient cooperative intelligence process 10 may prompt the salesclerk to inquire as to whether this family member travels to e.g., Countries A, B or C.

Additionally, as ambient cooperative intelligence process 10 may be monitoring the conversation between the family and the salesclerk, ambient cooperative intelligence process 10 may determine the quantity of cellular telephones they are interested in purchasing. Ambient cooperative intelligence process 10 may then review the various promotional plans being offered by the cell phone manufacturers, as well as any the available data plan options, so that ambient cooperative intelligence process 10 may present the phones and data plans that are most advantageous to the family.

Additionally, ambient cooperative intelligence process 10 may monitor the conversation between the family and the salesclerk to identify and/or correct any mistakes or misrepresentations that the salesclerk may have inadvertently made. For example, if the user said that they often travel to Country X and they are in the process of purchasing Cellular Telephone Y (which is not usable within Country X), ambient cooperative intelligence process 10 may covertly notify (e.g. via an earbud) the salesclerk that Cellular Telephone Y will not function properly within Country X.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method executed on a computing device comprising:
   generating a three-dimensional model of at least a portion of a three-dimensional space incorporating an ambient cooperative intelligence (ACI) system via a video recording subsystem of an ACI calibration platform;
   generating one or more audio calibration signals for receipt by an audio recording system included within the ACI system via an audio generation subsystem of the ACI calibration platform, wherein the one or more audio calibration signals includes the three-dimensional model of at least the portion of the three-dimensional space, wherein the video recording system of the ACI calibration platform identifies at least one of one or more stationary objects located within the three-dimensional space to define one or more interaction zones within the three-dimensional space, wherein the one or more interaction zones includes a first interaction zone proximate the at least one of the one or more stationary objects within the three-dimensional space; and
   autonomously positioning the ACI calibration platform within the three-dimensional space via a mobile base assembly of the ACI calibration platform based upon, at least in part, the at least one of one or more stationary objects defining the first interaction zone of the one or more interaction zones within the three-dimensional space of the three-dimensional model obtained from the video recording system of the ACI calibration platform.

2. The computer-implemented method of claim 1 wherein the video recording system of the ACI calibration platform is configured to interface with an object datasource that defines the at least one of one or more stationary objects located within the three-dimensional space.

3. The computer-implemented method of claim 1 further comprising:
autonomously cleaning at least a portion of the three-dimensional space via a cleaning assembly of the ACI calibration platform.

4. The computer-implemented method of claim 1 wherein the ACI calibration platform is configured to be manually positioned within the three-dimensional space.

5. The computer-implemented method of claim 1 wherein the three-dimensional model is further configured to define at least one of:
one or more subspaces within the three-dimensional space;
one or more objects within the three-dimensional space;
one or more features within the three-dimensional space; and
one or more noise sources within the three-dimensional space.

6. The computer-implemented method of claim 1 wherein the one or more audio calibration signals includes one or more of:
a noise signal;
a sinusoid signal; and
a multi-frequency signal.

7. A computer program product residing on a non-transitory computer readable medium having a plurality of instructions stored thereon which, when executed by a processor, cause the processor to perform operations comprising:
generating a three-dimensional model of at least a portion of a three-dimensional space incorporating an ambient cooperative intelligence (ACI) system via a video recording subsystem of an ACI calibration platform;
generating one or more audio calibration signals for receipt by an audio recording system included within the ACI system via an audio generation subsystem of the ACI calibration platform, wherein the one or more audio calibration signals includes the three-dimensional model of at least the portion of the three-dimensional space, wherein the video recording system of the ACI calibration platform identifies at least one of one or more stationary objects located within the three-dimensional space to define one or more interaction zones within the three-dimensional space, wherein the one or more interaction zones includes a first interaction zone proximate the at least one of the one or more stationary objects within the three-dimensional space; and
autonomously positioning the ACI calibration platform within the three-dimensional space via a mobile base assembly of the ACI calibration platform based upon, at least in part, the at least one of one or more stationary objects defining the first interaction zone of the one or more interaction zones within the three-dimensional space of the three-dimensional model obtained from the video recording system of the ACI calibration platform.

8. The computer program product of claim 7 wherein the video recording system of the ACI calibration platform is configured to interface with an object datasource that defines the at least one of one or more stationary objects located within the three-dimensional space.

9. The computer program product of claim 7 further comprising:
autonomously cleaning at least a portion of the three-dimensional space via a cleaning assembly of the ACI calibration platform.

10. The computer program product of claim 7 wherein the ACI calibration platform is configured to be manually positioned within the three-dimensional space.

11. The computer program product of claim 8 wherein the three-dimensional model is further configured to define at least one of:
one or more subspaces within the three-dimensional space;
one or more objects within the three-dimensional space;
one or more features within the three-dimensional space; and
one or more noise sources within the three-dimensional space.

12. The computer program product of claim 7 wherein the one or more audio calibration signals includes one or more of:
a noise signal;
a sinusoid signal; and
a multi-frequency signal.

13. An ambient cooperative intelligence (ACI) calibration platform comprising:
a video recording subsystem configured to generate a three-dimensional model of at least a portion of a three-dimensional space incorporating an ACI system;
an audio generation subsystem configured to generate one or more audio calibration signals for receipt by an audio recording system included within the ACI system, wherein the one or more audio calibration signals includes the three-dimensional model of at least the portion of the three-dimensional space, wherein the video recording system of the ACI calibration platform identifies at least one of one or more stationary objects located within the three-dimensional space to define one or more interaction zones within the three-dimensional space, wherein the one or more interaction zones includes a first interaction zone proximate the at least one of the one or more stationary objects within the three-dimensional space; and
a mobile base assembly configured to autonomously position the ACI calibration platform within the three-dimensional space based upon, at least in part, the at least one of one or more stationary objects defining the first interaction zone of the one or more interaction zones within the three-dimensional space of the three-dimensional model obtained from the video recording system of the ACI calibration platform.

14. The ACI calibration platform of claim 13 wherein the video recording system of the ACI calibration platform is further configured to interface with an object datasource that defines the at least one of one or more stationary objects located within the three-dimensional space.

15. The ACI calibration platform of claim 13 further comprising:
a cleaning assembly configured to autonomously clean at least a portion of the three-dimensional space.

16. The ACI calibration platform of claim 13 wherein the ACI calibration platform is configured to be manually positioned within the three-dimensional space.

17. The ACI calibration platform of claim 13 wherein the three-dimensional model is further configured to define at least one of:

one or more subspaces within the three-dimensional space;
one or more objects within the three-dimensional space;
one or more features within the three-dimensional space; and
one or more noise sources within the three-dimensional space.

18. The ACI calibration platform of claim 13 wherein the one or more audio calibration signals includes one or more of:
a noise signal;
a sinusoid signal; and
a multi-frequency signal.

* * * * *